(12) United States Patent
Sando et al.

(10) Patent No.: US 8,021,629 B2
(45) Date of Patent: Sep. 20, 2011

(54) ANALYZER

(75) Inventors: Yasuhiro Sando, Amagasaki (JP); Akihisa Nakajima, Sagamihara (JP); Kusunoki Higashino, Osaka (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 206 days.

(21) Appl. No.: 11/378,516

(22) Filed: Mar. 17, 2006

(65) Prior Publication Data

US 2006/0213291 A1 Sep. 28, 2006

(30) Foreign Application Priority Data

Mar. 24, 2005 (JP) ................................. 2005-086684
Mar. 25, 2005 (JP) ................................. 2005-089247
Mar. 29, 2005 (JP) ................................. 2005-094612

(51) Int. Cl.
*G01N 35/00* (2006.01)

(52) U.S. Cl. ........ 422/505; 422/502; 422/504; 422/400; 422/63; 422/81; 436/180

(58) Field of Classification Search .................... 422/63, 422/67, 81, 99, 101, 104; 436/180, 43; 204/601–603
See application file for complete search history.

(56) References Cited

U.S. PATENT DOCUMENTS

| | | | | |
|---|---|---|---|---|
| 5,519,635 A * | 5/1996 | Miyake et al. | ................. | 700/285 |
| 6,240,790 B1 * | 6/2001 | Swedberg et al. | ......... | 73/863.21 |
| 6,358,387 B1 * | 3/2002 | Kopf-Sill et al. | ............. | 204/603 |
| 6,368,079 B2 * | 4/2002 | Peters et al. | ................ | 417/413.2 |
| 6,383,452 B1 * | 5/2002 | Miyake et al. | ................... | 422/63 |
| 2002/0164824 A1 * | 11/2002 | Xiao et al. | ..................... | 436/524 |
| 2004/0200724 A1 * | 10/2004 | Fujii et al. | ..................... | 204/601 |
| 2006/0239862 A1 * | 10/2006 | Nakajima et al. | ............. | 422/100 |
| 2006/0263914 A1 * | 11/2006 | Sando et al. | ..................... | 438/14 |
| 2007/0053795 A1 * | 3/2007 | Laugharn et al. | ............... | 422/99 |
| 2008/0112851 A1 * | 5/2008 | Higashino et al. | ........... | 422/68.1 |
| 2008/0131327 A1 * | 6/2008 | Van Dam et al. | ............. | 422/103 |
| 2009/0010820 A1 * | 1/2009 | Fehm et al. | .................... | 422/189 |

FOREIGN PATENT DOCUMENTS

| | | |
|---|---|---|
| JP | 2001-322099 A | 11/2001 |
| JP | 2004-108285 A | 4/2004 |
| JP | 2006-121934 A | 5/2006 |
| JP | 2006-121935 A | 5/2006 |
| WO | WO 2005/107937 | * 11/2005 |

* cited by examiner

*Primary Examiner* — Kathryn Wright

(74) *Attorney, Agent, or Firm* — Holtz, Holtz, Goodman & Chick PC

(57) ABSTRACT

An analyzer for analysis of a specimen in a testing chip that includes a micropump connecting section that is connected with a micropump to take in liquid from the micropump and includes a micro flow channel in which a reagent and the specimen are mixed so as to react with each other, the analyzer including: a mounting section for mounting the testing chip attachably and detachably thereto; a micropump unit that has a testing chip connecting section to be connected with the micropump connecting section of the testing chip which is mounted on the mounting section, and feeds liquid to the testing chip through the testing chip connecting section; and a pressing mechanism that presses the micropump connecting section and the testing chip connecting section against each other, the connecting sections being connected with each other.

24 Claims, 20 Drawing Sheets

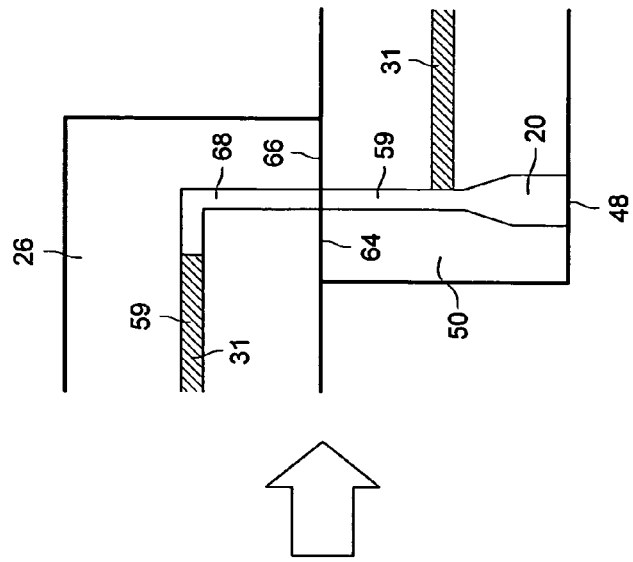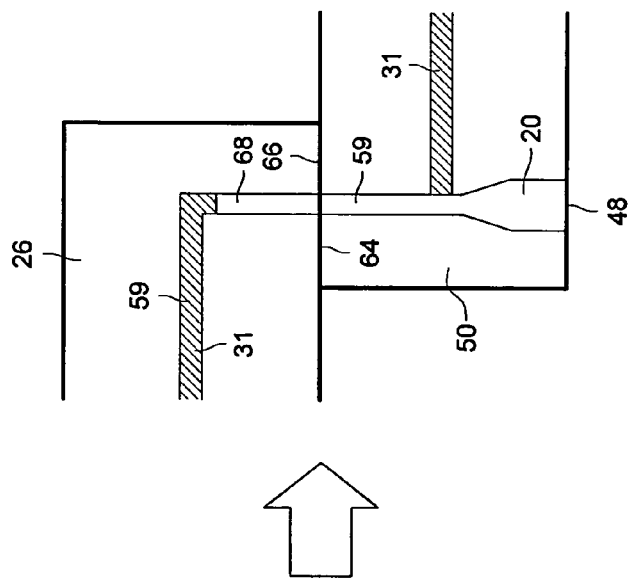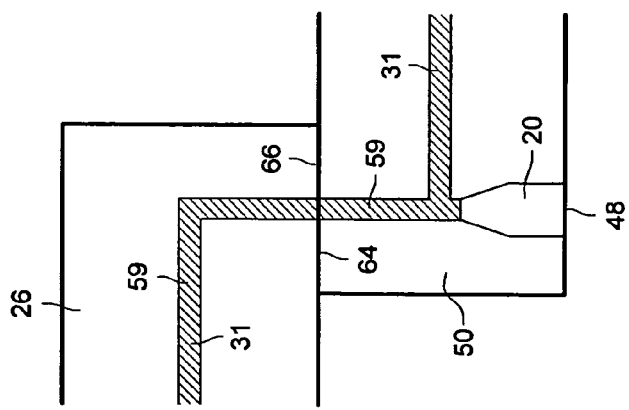

FIG. 18 (a-1)
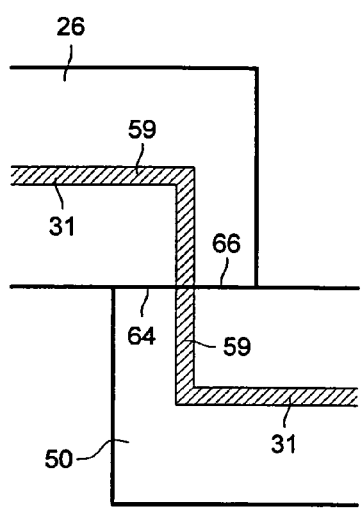
FIG. 18 (a-2)
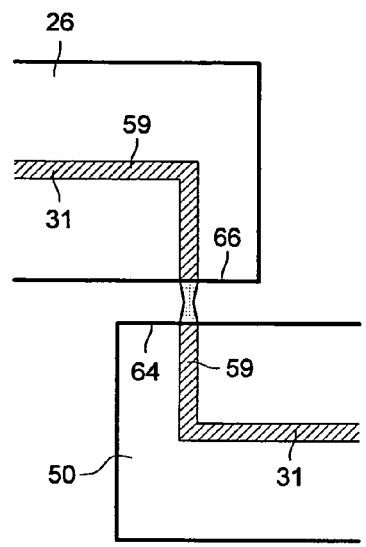
FIG. 18 (b-1)
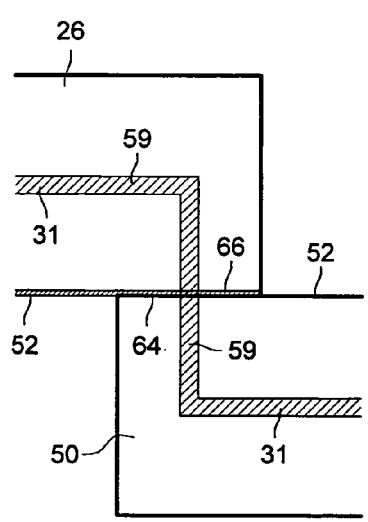
FIG. 18 (b-2)
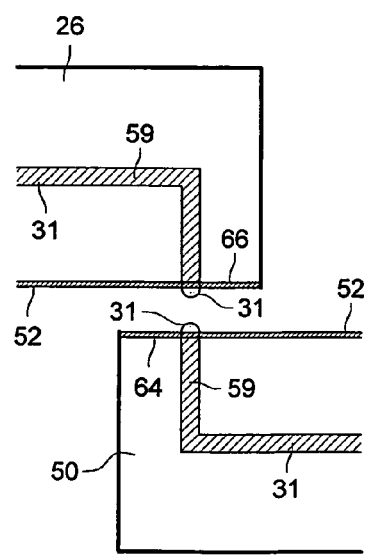

ANALYZER

This application is based on Japanese Patent Applications No. 2005-086684 filed on Mar. 24, 2005, No. 2005-089247 filed on Mar. 25, 2005 and No. 2005-094612 filed on Mar. 29, 2005 in Japanese Patent Office, the entire contents of which are hereby incorporated by reference.

FIELD OF THE INVENTION

The present invention relates to an analyzer onto which loaded is an testing chip wherein there are formed a series micro flow channels where mixing of a bio-material contained in a specimen and a reagent, reaction thereof and detection of the reaction are conducted, and conducts mixing of bio-material contained in a specimen and a reagent, reaction thereof and detection of the reaction automatically, while conducting liquid feeding in the micro flow channels of the testing chip with a micro-pump unit.

BACKGROUND OF THE INVENTION

In recent years, there has been developed a system wherein devices and means (for example, pumps, valves, channels and sensors) for conducting conventional sample preparation, chemical analysis and chemical synthesis are miniaturized and integrated on one chip, by using micromachine technology system and hyperfine processing technique freely.

This system is also called μ-TAS (Micro Total Analysis System), a bio-reactor, a Lab-on-chip (Lab-on-chips) or a biochip, and its application is expected in medical testing/analysis fields, environmental measurement fields and agricultural products manufacturing fields.

As is observed in genetic testing, in particular, when complicated processes, skilled craft and operations of equipment are required, a micro-reactor representing an automated, accelerated and simplified minimized analysis system has the greatest effects resulting from cost, an amount of necessary samples and time required and also resulting from analyses which can cope with any time and any place.

Even in measurement in a micro-reactor of a chip type capable of producing results promptly independently of a place, quantitativity and accuracy of analysis are emphasized, in the job site where various examinations including a clinical examination are made.

Further, since there are strict restrictions in terms of a size and a form for the micro-reactor, it is necessary to establish a liquid feeding system having a simple structure and high reliability.

The inventors of the invention have already proposed a micro-overall-analysis system which is suitable for gene amplification reaction and its detection (Patent Document 1-Patent Document 6).

Further, the inventors of the invention have already proposed a micro-pump system which is suitable for a micro-fluid-control element that has high accuracy and is excellent in reliability (Patent Document 7 and Patent Document 8).

(Patent Document 1) TOKUGAN No. 2004-138959
(Patent Document 2) TOKUGAN No. 2004-169912
(Patent Document 3) TOKUGAN No. 2004-310744
(Patent Document 4) TOKUGAN No. 2004-312313
(Patent Document 5) TOKUGAN No. 2004-312314
(Patent Document 6) TOKUGAN No. 2004-312315
(Patent Document 7) TOKUKAI No. 2001-322099
(Patent Document 8) TOKUKAI No. 2004-108285

In the micro-overall-analysis system aforementioned, liquid such as a reagent in a micro flow channel of the testing chip is sent by a micro-pump.

Specifically, with respect to a micro-pump unit having a plurality of pumps in a chip each pump employing a piezoelectric element in the structure disclosed in each of Patent Documents 7 and 8, and with respect to an testing chip, channels on the pump side and channels on the testing chip side are communicated each other by making a chip surface of the micro-pump unit and a chip surface of the testing chip be in tight contact with each other and the channel openings of the both fit with each other.

However, if contact surfaces are wet before connection, at the connecting section between the micro-pump unit and the testing chip, there is a possibility that a liquid, such as a driving liquid, that passes through the connecting section from the micro-pump side to the testing chip side leaks out of a clearance between these contact surfaces, when the pump unit and the chip are used.

SUMMARY OF THE INVENTION

When liquid-tightness is not sufficient in the connecting section between the micro-pump unit and the testing chip, there is also a possibility of entry of contamination into a channel from the outside.

In view of this circumstance, an object of the invention is to provide an analyzer wherein sufficient and tight contact can surely be secured between the connecting section of a micro-pump unit and the connecting section of a testing chip, and liquid leakage from the channel or entry of contamination can be prevented.

In a first aspect of the invention, there is provided an analyzer for analysis of a specimen in a testing chip that includes a micropump connecting section that is connected with a micropump to take in liquid from the micropump and includes a micro flow channel in which a reagent and the specimen are mixed so as to react with each other, the analyzer including: a mounting section for mounting the testing chip attachably and detachably thereto; a micropump unit that has a testing chip connecting section to be connected with the micropump connecting section of the testing chip which is mounted on the mounting section, and feeds liquid to the testing chip through the testing chip connecting section; and a pressing mechanism that presses the micropump connecting section and the testing chip connecting section against each other, the connecting sections being connected with each other.

In a second aspect of the invention, the analyzer in the first aspect of the invention further includes a gas blower that sends gas to a connecting part between the micropump connecting section of the testing chip and the testing chip connecting section of the micropump unit when the micropump connecting section of the testing chip and the testing chip connecting section of the micropump unit are separated from each other, wherein the micropump unit includes a flow channel to take in the gas sent out from the gas blower.

In a third aspect of the invention, the analyzer in the first aspect of the invention further includes a cleaning mechanism that cleans the micropump connecting section of the testing chip and/or the testing chip connecting section of the micropump unit.

BRIEF DESCRIPTION OF THE DRAWINGS

FIGS. 16(a) to 16(c) are schematic diagrams illustrating movement of a liquid in the case of using a gas blower of the micro-overall system of the invention shown in FIG. 3;

FIGS. 18(a-1), 18(a-2), 18(b-1), and 18(b-2) are schematic diagrams illustrating the circumstance wherein the testing chip and the micro-pump unit are separated each other in a micro-overall system of the invention and in a known micro-overall system;

DETAILED DESCRIPTION OF PREFERRED EMBODIMENT

Figure 1:
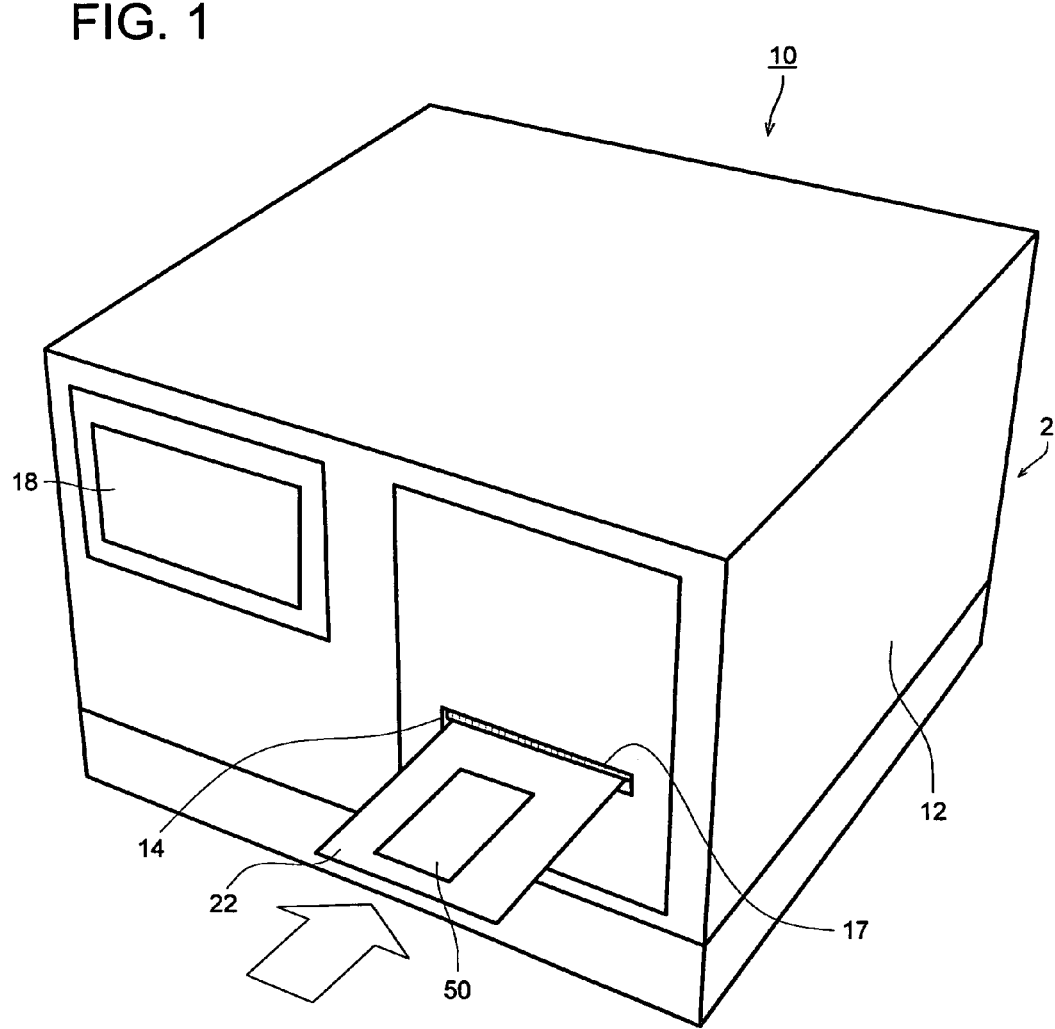
FIG. 1 is a schematic perspective view showing an example of a micro-overall-analysis system of the invention.

The present invention includes the following structures.

(Structure 1)

A micro-overall-analysis system includes the following item (A) and M.

(A) An testing chip which is structured by a laminate and includes a specimen storage section that stores a specimen to be an object of testing, a reagent storage section that stores a reagent to be added to the specimen, a micro flow channel in which the specimen stored in the specimen storage section and the reagent stored in the reagent storage section are mixed, a micropump connecting section on the upstream side in the flowing direction of fluid in the testing chip, and a test fluid detection section on the downstream side in the flowing direction of the fluid in the testing chip.

(B) A specimen analyzer that automatically detects information inside the testing chip if the testing chip is attachably and detachably mounted to the analyzer.

Herein, the micro-overall-analysis system including (A) and (B) includes a pressing mechanism to promote prevention of leaking of liquid and improve thermal conduction efficiency.

In the micro-overall-analysis system having the above structure that is equipped with a pressing means, it is possible to actively prevent generation of liquid leakage, and to correctly conduct temperature adjustment by a temperature control device.

(Structure 2)

In the micro-overall-analysis system of Structure 1, the specimen analyzer includes a testing chip connecting section having a flow channel opening to feed a drive liquid into the testing chip, a detection unit to detect information contained in a mixed liquid in the testing chip, a temperature controller to set the temperature of a predetermined portion of the testing chip to a predetermined temperature, and a pump unit to feed the drive liquid to the micropump connecting section of the testing chip. Herein, the pressing mechanism is preferably arranged at the detection unit, the temperature controller, the pump unit, or a conveying tray to load the testing chip.

(Structure 3)

The micro-overall-analysis system of Structure 2, wherein the pressing mechanism is preferably implemented by a detection section that detects reaction in the micro flow channel, the temperature controller, the micropump unit, or the conveying tray, each itself.

With such a structure, it is possible to construct a pressing mechanism effectively by using existing members.

(Structure 4)

The micro-overall-analysis system of Structure 2, wherein the pressing mechanism is preferably structured by a member different from the detection section, the temperature controller, the micropump unit, and the conveying tray.

Even in the case of this structure, a pressing mechanism can be constructed.

(Structure 5)

The micro-overall-analysis system of Structure 2, wherein the pressing mechanism is preferably disposed between one of the detection section, the temperature controller and the micropump unit, and the conveying tray.

(Structure 6)

The micro-overall-analysis system of any one of Structures 1 to 5, wherein the pressing mechanism preferably includes a positioning structure.

Since such a structure makes it possible to guide the testing chip to the right position constantly; it is possible to make the pressing mechanism to function preferably.

(Structure 7)

The micro-overall-analysis system of any one of Structures 1 to 6, wherein the pressing mechanism is preferably used with a compressive and deformable sheet member.

With such a structure, a sheet member is tightened, and liquid leakage can be prevented accordingly.

(Structure 8)

The micro-overall-analysis system of Structure 1, wherein the pressing mechanism is preferably structured such that the testing chip connecting section and the conveying tray in the specimen analyzer are sandwiched by a member.

With such a structure, it is also possible to construct a pressing means with operations from the outside, by pressing with pins from the both sides, or by using an electro-magnet.
(Structure 9)

The micro-overall-analysis system of Structure 6, wherein the positioning structure is preferably guided in moving by a guide groove formed on either the testing chip or the specimen analyzer.

A positioning unit having such a structure makes it possible to guide to a predetermined position with a simple structure.
(Structure 10)

The micro-overall-analysis system of Structure 6, wherein the positioning structure is preferably arranged with holes formed through the testing chip and the analyzer and pin members to be inserted in the holes.

Such a structure makes it possible to conduct positioning by inserting a pin into a hole, and to release engagement of positioning by pulling out the pin.
(Structure 11)

The micro-overall-analysis system of Structure 6, wherein the positioning structure is preferably arranged with a notch formed on a portion of a side of the testing chip and a protrusion provided at the analyzer.

Even in the case of, this structure, a positioning unit can be constructed by the relatively simple structure.
(Structure 12)

A micro-overall-analysis system includes the following item (A) and (B).
(A) A testing chip includes a series of micro flow channels in which a biological material, to be an object of measuring, contained in a specimen or in a processed liquid produced by processing the specimen in a flow channel, and a reagent stored in a reagent storage section, are fed into a flow channel as a reaction section and mixed in it, then these react with each other, and a produced material by the reaction or a further processed material of it is sent to a flow channel for a detection section. The testing chip further includes a pump connecting section having a flow channel opening to communicate with a micropump.
(B) A system main body, namely a specimen analyzer, includes a base main body and a micropump unit in the base main body, the micropump unit including a plurality of micropumps and a testing chip connecting section having flow channel openings to communicate with the testing chip.

In this micro-overall-analysis system, the testing chip is mounted in the base main body in such a manner that a pump connecting section of the testing chip and a testing chip connecting section of the micropump unit are in a liquid-tight contact with each other, and the reaction between the biologic material and the reagent in the testing chip and detection of it are automatically performed.

This micro-overall-analysis system includes a gas blower that sends gas to the connecting part between the micropump connecting section of the testing chip and the testing chip connecting section of the micropump unit, when the micropump connecting section of the testing chip and the testing chip connecting section of the micropump unit are separated from each other, wherein the testing chip or the micropump unit includes a flow channel to take in the gas sent out from the gas blower.

If the structure is arranged in this way, a driving liquid in a channel near the connection between the pump connecting section and the testing chip connecting section can be pushed out of the vicinity of the connection, by gas that is fed out of an gas-blower and is introduced from a channel provided on the testing chip or on the micro-pump unit.

Thus, it is possible to prevent that a liquid flows out of the connection area when the micro-pump unit and the testing chip are separated from each other.
(Structure 13)

A micro-overall-analysis system includes the following item (A) and (B).
(A) A testing chip includes a series of micro flow channels in which a biological material, to be an object of measuring, contained in a specimen or in a processed liquid produced by processing the specimen in a flow channel, and a reagent stored in a reagent storage section, are fed into a flow channel as a reaction section and mixed in it, then these react with each other, and a produced material by the reaction or a further processed material of it is sent to a flow channel for a detection section. The testing chip further includes a pump connecting section having a flow channel opening to communicate with a micropump.
(B) A system main body, namely a specimen analyzer, includes a base main body and a micropump unit in the base main body, the micropump unit including a plurality of micropumps and a testing chip connecting section having flow channel openings to communicate with the testing chip.

In this micro-overall-analysis system, the testing chip is mounted in the base main body in such a manner that a pump connecting section of the testing chip and a testing chip connecting section of the micropump unit are in a liquid-tight contact with each other, and the reaction between the biologic material and the reagent in the testing chip and detection of it are automatically performed.

This micro-overall-analysis system includes a gas blower that sends gas to the connecting part between the micropump connecting section of the testing chip and the testing chip connecting section of the micropump unit, when the micropump connecting section of the testing chip and the testing chip connecting section of the micropump unit are separated from each other, wherein the testing chip and the micropump unit includes a flow channel to take in the gas sent out from the gas blower.

If the structure is arranged in this way, a driving liquid in a channel near the connection between the pump connecting section and the testing chip connecting section can be pushed out of the vicinity of the connection, by gas that is fed out of an gas-blower and is introduced from channels provided on the testing chip and on the micro-pump unit.

Thus, it is possible to prevent that a liquid flows out of the connection when the micro-pump unit and the testing chip are separated from each other.

Further, if a channel for introducing gas fed out of an gas-blower is provided on each of both sides of the testing chip and micro-pump unit, it is possible to make the gas to flow in from any direction, and thereby, to push out surely a driving liquid in the channel near the connection between the pump connecting section and the testing channel connecting section to the outside of the vicinity of the connection.
(Structure 14)

The micro-overall-analysis system of Structure 13 preferably includes a liquid collection device that recovers liquid that has been pushed outside the micropump unit or the testing chip by the gas sent out from the gas blower.

By constructing in this way, a liquid pushed out to the outside of the micro-pump unit or of the testing chip can be collected surely without scattering into the system main body.
(Structure 15)

In the micro-overall-analysis system of any one of Structures 12 to 14, the gas blower is preferably provided in a vicinity of the micropump connecting section of the testing chip or a vicinity of the testing chip connecting section of the micropump unit.

By constructing in this way, it is possible to prevent that the apparatus is complicated in the system main body, because gas can be taken directly in the channel of the testing chip.
(Structure 16)

In the micro-overall-analysis system of any one of Structures 12 to 14, the gas blower is preferably provided in a vicinity of the micropump connecting section of the testing chip and a vicinity of the testing chip connecting section of the micropump unit.

By constructing in this way, it is possible to prevent that the apparatus is complicated in the system main body, because gas can be taken directly in the channel of the testing chip.
(Structure 17)

A micro-overall-analysis system includes the following item (A) and (B).
(A) A testing chip includes a series of micro flow channels in which a biological material, to be an object of measuring, contained in a specimen or in a processed liquid produced by processing the specimen in a flow channel, and a reagent stored in a reagent storage section, are fed into a flow channel as a reaction section and mixed in it, then these react with each other, and a produced material by the reaction or a further processed material of it, is sent to a flow channel for a detection section. The testing chip further includes a pump connecting section having a flow channel opening to communicate with a micropump.
(B) A system main body, namely a specimen analyzer, includes a base main body and a micropump unit in the base main body, the micropump unit including a plurality of micropumps and a testing chip connecting section having flow channel openings to communicate with the testing chip.

In this micro-overall-analysis system, the testing chip is mounted in the base main body in such a manner that a pump connecting section of the testing chip and a testing chip connecting section of the micropump unit are in a liquid-tight contact with each other, and the reaction between the biologic material and the reagent in the testing chip and detection of it are automatically performed.

This micro-overall-analysis system is provided with a hydrophobic layer on a surface of the pump connecting section of the testing chip and on a surface of the testing chip connecting section of the micropump unit.

If a hydrophobic layer is provided on each surface of the pump connecting section of the testing chip and the testing chip connecting section of the micro-pump unit, it is possible to prevent that a liquid such as a driving liquid congregates under a surface tension and scatters to locations other than the connection, when the testing chip and the micro-pump unit are separated from each other.
(Structure 18)

In the micro-overall-analysis system of Structure 17, the hydrophobic layer is preferably made of any one of polyethylene, silicone and Teflon (a registered trademark).

By constructing in this way, it is possible to prevent that a liquid such as a driving liquid congregates under a surface tension and scatters to locations other than the connection, when the testing chip and the micro-pump unit are separated from each other.
(Structure 19)

In the micro-overall-analysis system of any one of Structures 12 to 18, the system main body preferably includes a detection device that optically detects a reaction in a flow channel as a detection section after a biologic material and a reagent have reacted with each other in a micro flow channel in the testing chip, a pump controller to control liquid feeding by the micropumps, and a temperature controller to control the temperature of a predetermined part of the testing chip.

By constructing in this way, it is possible to conduct desired test surely of a specimen in the system main body.
(Structure 20)

In the micro-overall-analysis system of any one of Structures 12 to 19, a micropump preferably includes a first flow channel of which flow resistance varies with a differential pressure, a second flow channel of which variation rate of a flow resistance to variation in a differential pressure is smaller than that of the first flow channel, a pressing chamber connected with the first flow channel and the second flow channel, and an actuator that changes an inner pressure of the pressing chamber.

By constructing in this way, it is possible to take a driving liquid in the testing chip surely.

It is therefore possible to surely conduct desired test of a specimen in the system main body.
(Structure 21)

A micro-overall-analysis system includes the following item (A) and (B).
(A) A testing chip includes a series of micro flow channels in which a biological material, to be an object of measuring, contained in a specimen or in a processed liquid produced by processing the specimen in a flow channel, and a reagent stored in a reagent storage section, are fed into a flow channel as a reaction section and mixed in it, then these react with each other, and a produced material by the reaction or a further processed material of it is sent to a flow channel for a detection section. The testing chip further includes a pump connecting section having a flow channel opening to communicate with a micropump.
(B) A system main body, namely an analyzer for analysis of specimen, includes a base main body and a micropump unit in the base main body, the micropump unit including a plurality of micropumps and a testing chip connecting section having flow channel openings to communicate with the testing chip.

In this micro-overall-analysis system, the testing chip is mounted in the base main body in such a manner that a pump connecting section of the testing chip and a testing chip connecting section of the micropump unit are in a liquid-tight contact with each other, and the reaction between the biologic material and the reagent in the testing chip and detection of it are automatically performed.

In this micro-overall-analysis system, the base main body is preferably provided with a cleaning mechanism that cleans the micropump connecting section of the testing chip and/or the testing chip connecting section of the micropump unit.

By constructing in this way, the connecting sections of the testing chip and the micro-pump unit are subjected to close contact, after being cleaned by a cleaning mechanism, which makes it possible to prevent liquid leakage that can happen when a contact surface of the connecting section is wet, or it is contaminated with foreign substances.
(Structure 22)

In the micro-overall-analysis system of Structure 21, preferably, the cleaning mechanism is a wiping device that wipes off foreign matter and/or liquid on a surface of the micropump connecting section of the testing chip and/or a surface of the testing chip connecting section of the micropump unit.
(Structure 23)

In the micro-overall-analysis system of Structure 21, preferably, the cleaning mechanism is a gas blower that removes foreign matter and/or liquid on a surface of the micropump connecting section of the testing chip and/or a surface of the testing chip connecting section of the micropump unit by sending gas.

(Structure 24)

In the micro-overall-analysis system of any one of Structures 21 to 23, the cleaning mechanism is preferably provided at a testing chip gateway for introducing the testing chip into the base main body.

(Structure 25)

In the micro-overall-analysis system of any one of Structures 21 to 23, the cleaning mechanism is preferably provided in a vicinity of a connecting part between the testing chip and the micropump unit in the base main body.

(Structure 26)

In the micro-overall-analysis system of any one of Structures 21 to 25, the system main body preferably includes a detection device that optically detects a reaction in a flow channel as a detection section after a biologic material and a reagent have reacted with each other in a micro flow channel in the testing chip, a pump controller to control liquid feeding by the micropumps, and a temperature controller to control the temperature of a predetermined part of the testing chip.

(Structure 27)

In the micro-overall-analysis system of any one of Structures 21 to 26, a micropump preferably includes a first flow channel of which flow resistance varies with a differential pressure, a second flow channel of which variation rate of a flow resistance to variation in a differential pressure is smaller than that of the first flow channel, a pressing chamber connected with the first flow channel and the second flow channel, and an actuator that changes an inner pressure of the pressing chamber.

In a micro-overall-analysis system in accordance with the invention in the example of structure of the invention which has been described, it is possible to secure sufficient and tight contact between the micro-pump unit on the specimen analyzer side and the micro-pump connecting section of the testing chip. It is therefore possible to prevent generation of contamination, not to mention liquid leakage from a channel. Further, by pressurizing the temperature control device, a temperature at a predetermined part of the testing chip can easily be adjusted.

Examples of the invention will be explained as follows, referring to the drawings.

Figure 2:
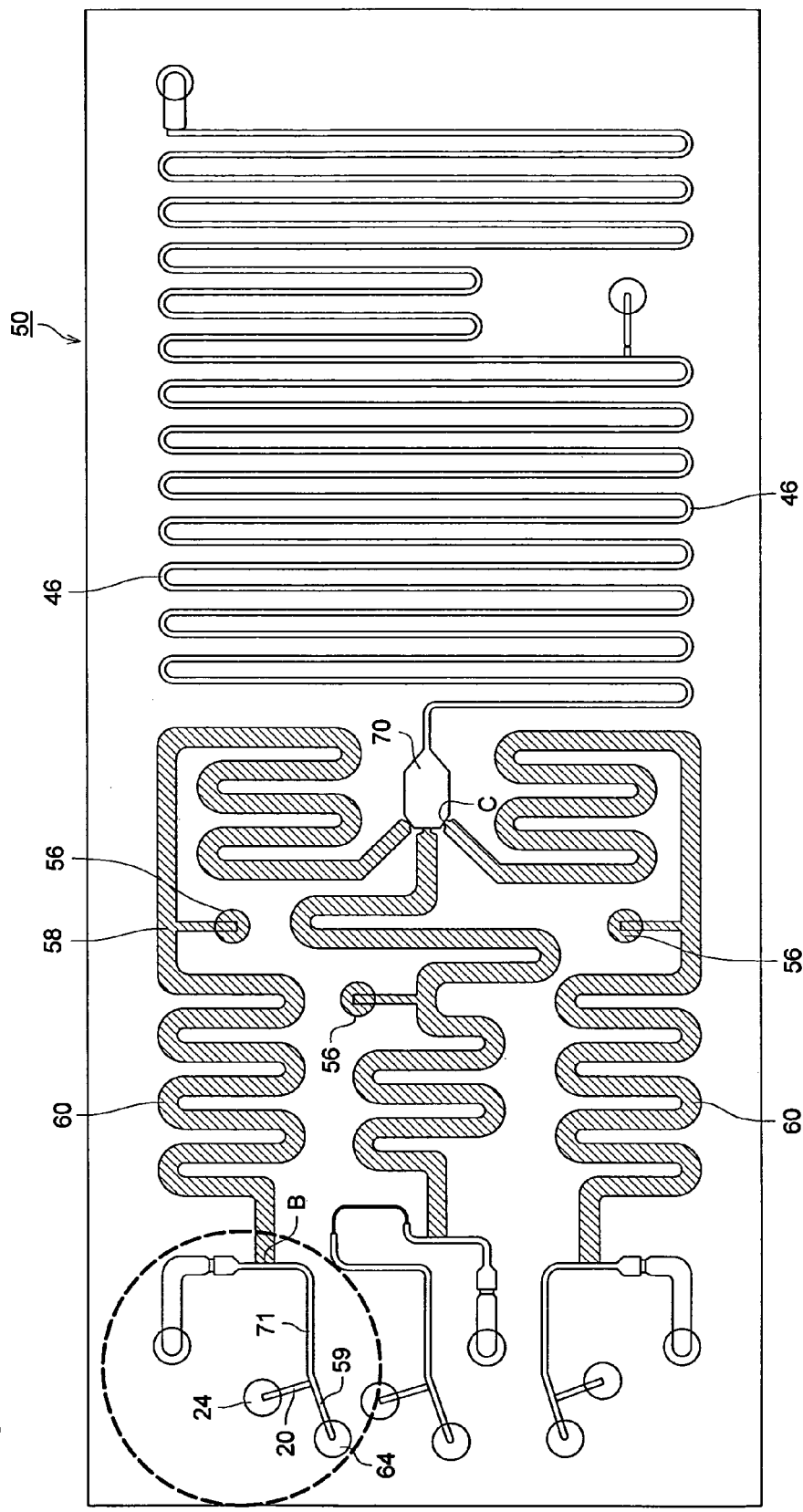
FIG. 2 is a schematic diagram illustrating a testing chip for a micro-overall-analysis system of the invention.
Figure 3:
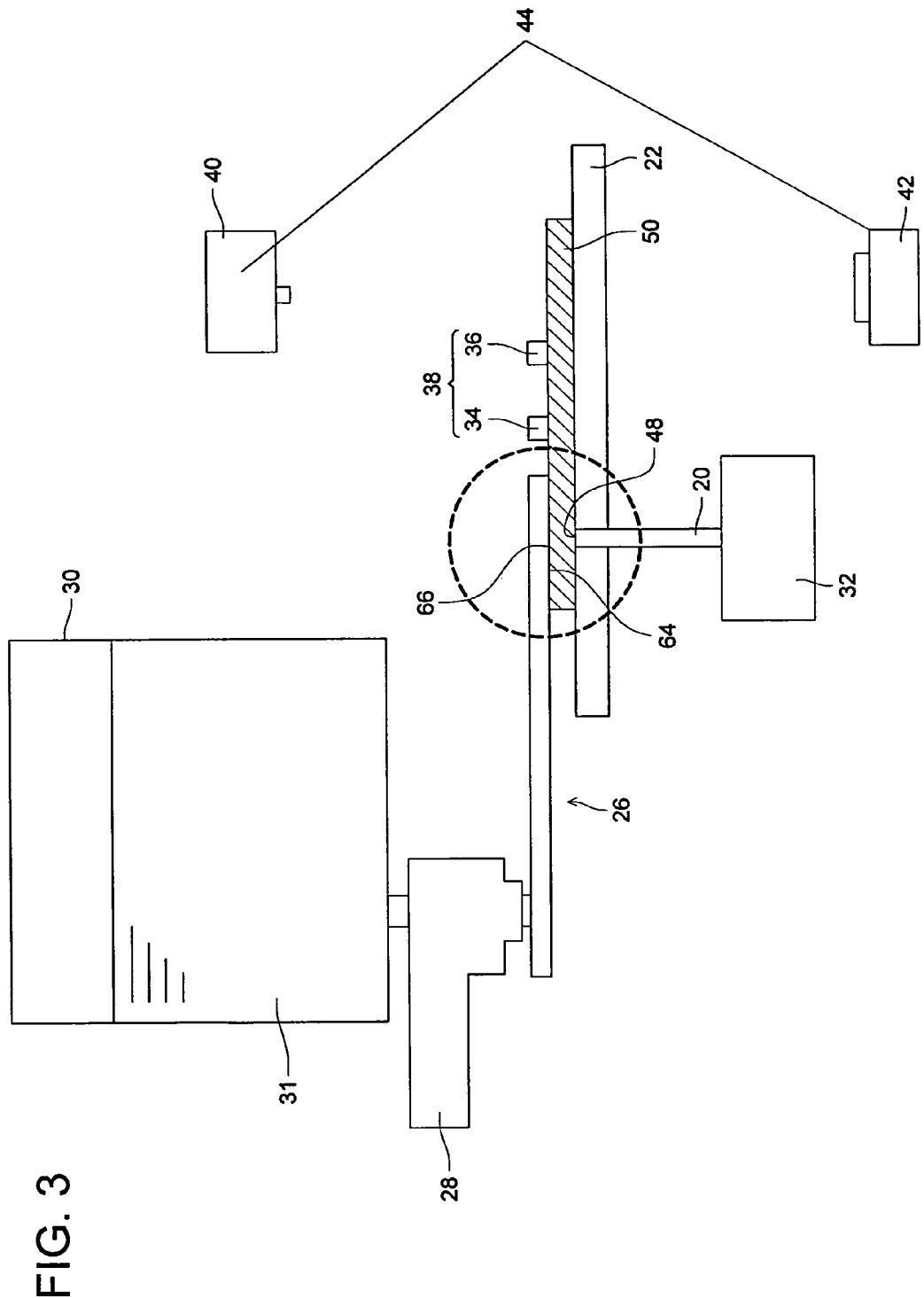
FIG. 3 is a schematic diagram of the inside of a base main body showing how an testing chip is loaded on the base main body of the micro-overall-analysis system in the example.

Micro-overall-analysis system 10, shown in each of FIG. 1-FIG. 3 includes a system main body, namely an analyzer for analysis of specimen, for which micro-pump unit 26, pump control device 28, temperature control device 38 and detecting device 44 are housed in base main body 12 and includes testing chip 50.

(Testing Chip)

Testing chip 50 whose outline is shown in FIG. 2 is equipped with reagent storage sections 60 (hatched portions in FIG. 5) in each of which reagent 58 is sealed in advance, and equipped with channel 46, which is a detection section, leading to the downstream side from the reagent storage sections 60.

Incidentally, the reagent 58 is one to be supplied through reagent supply hole 56, and when the reagent 58 is supplied into the testing chip 50, the reagent 58 is filled in the storage section up to the points immediately before water-repellent valves B and C.

Further, at the downstream side of these reagent storage sections 60, a plurality of reagent storage sections 60 merge at merging point 70, and micro flow channel 46 is provided after the merging point.

At the downstream side of this micro flow channel 46, there is provided an unillustrated specimen storage section, and specimen held in the specimen storage section and a liquid which is a mixture of plural reagents 58 passing through the micro flow channel 46 are mixed are further mixed, in the structure.

On the reagent storage sections 60 of the testing chip 50, valve portions such as water-repellent valves are arranged at proper positions, to control, for example, quantification of an amount of liquid to be sent and to control mixing of respective liquids.

At the upstream side of the reagent storage section 60 of the testing chip 50, there are provided pump-connecting section 64 for connecting to chip-connecting section 66 of micropump unit 26 shown in FIG. 3 and gas-blower-connecting section 24 for connecting to gas-blower 32 which will be described later.

Testing chip 50 is one constructed so that gene amplification reaction by ICAN method in the chip and automatic detection thereof and simultaneous gene diagnosis for plural genes may be carried out by injecting gene specimen extracted from blood or from spat phlegm. This testing chip 50 is a chip whose longitudinal length and lateral length are in several centimeters, and in its structure, amplification reaction and its detection can be carried out automatically, simply by dropping a blood specimen of about 2-3 µL in this chip, for example, and by mounting it on specimen analyzer 2.

The testing chip 50 is one formed with a laminated body wherein appropriate members of resin, glass, silicon or ceramic are combined, and it is preferably formed with plastic resin for which processing is easy, cost is low and incineration dumping is easy.

For example, polystyrene resin is excellent in moldability, and it has strong tendency to adsorb streptoavidin, whereby, a detection region can be formed easily in a micro flow channel. In addition, the surface of the testing chip 50 needs to be transparent, for the purpose of detecting optically fluorescent materials or product materials showing color reactions.

The testing chip 50 of this kind is a piece of chip made by combining properly one or more members of plastic resin, glass, silicon and ceramic.

Micro flow channel 46 of the testing chip 50 and a frame body are preferably formed from plastic resin for which processing is easy, cost is low and incineration dumping is easy.

For example, polystyrene resin is excellent in moldability, and it has strong tendency to adsorb streptoavidin, whereby, a detection region can be formed easily on a micro flow channel.

Incidentally, the micro flow channel is formed to be about 10 µm-several hundred µm in terms of a width and a depth.

Further, for the purpose of detecting optically fluorescent materials or product materials showing color reactions, it is necessary that at least a detection section, covering detection region of the micro flow channel of the surface of the testing chip 50 is a transparent member, or preferably transparent plastic.

Typically, respective reagents 58 held in plural reagent storage sections 60 are mixed in the reagent storage section 60 at the downstream side, and mixed reagents in respective reagent storage sections 60 are further merged at the merging point 70 to be sent to micro flow channel 46 at the downstream side.

At the downstream side of the micro flow channel 46, specimen and mixed reagent are merged and mixed from Y-shaped channel, which is not illustrated, and then, reactions are started when temperature rises, and reactions are detected by the detection region provided on the channel.

The system of the invention can be used favorably, especially for the test of genes or of nucleic acid.

In this case, micro flow channel 46 of the testing chip 50 is made to be of the structure suitable for PCR amplification, and the basic channel structure can be substantially the same even for biological materials other than those for genetic testing.

Usually, it is only required to change specimen preprocessing sections, reagents and probes, and in this case, arrangement and number of liquid-feeding elements may be changed.

Those skilled in the art can change the types of analyses easily, by putting necessary reagents into the testing chip 50 for an immunoassay method, and by making a modification including some changes of channel element and specification changes.

Bio-materials other than genes mentioned here mean various types of metabolites, hormone and protein (including an enzyme and an antigen).

In an preferred embodiment of the testing chip 50, there are provided a specimen storage section in which a specimen or analite substance. (for example, DNA) extracted from the specimen is injected in one chip, a specimen preprocessing section that conducts preprocessing of the specimen, a reagent storage section that holds a reagent to be used for a probe combination reaction and a detection reaction (including also a gene amplification reaction or an antigen-antibody reaction), a positive control storage section that holds a positive control, a negative control storage section that holds a negative control, a probe storage section that holds a probe (for example, a probe to hybridize to a gene to be detected that is amplified by a gene amplification reaction), a micro flow channel that is communicated with respective storage sections and a pump-connecting section that can be connected to a separate micro-pump 21 capable of feeding liquids in the respective storage sections and the channel.

To the testing chip 50, there is connected a micro-pump 21 through pump-connecting section 64, and thereby, a specimen held in a specimen storage section (not shown) or a biomaterial extracted from the specimen (for example, DNA or other bio-materials) and reagent 58 held in reagent storage section 60 are sent to merging point 70 which is located at the downstream side of the reagent storage section 60, and are further mixed to react at a reaction region of the micro flow channel 46, for example, at a region of gene amplification reaction (an antigen-antibody reaction, in the case of protein), then, a processing liquid having processed the reacted liquid and a probe held in a probe storage section are sent to a detection section located in the channel at the downstream side thereof so that the processing liquid may be combined with the probe (or may be hybridized), thus, the bio-material is detected based on this reactive product.

Further, in the same way as in the foregoing, the reaction and detection are conducted even for positive control held in the positive control storage section and negative control held in the negative control storage section.

A specimen storage section (not shown) in the testing chip 50 is communicated with a specimen injecting section which holds a specimen temporarily and supplies the specimen to a mixing section.

It is desirable that the specimen injecting section through which the specimen is injected into the specimen storage section from its upper side is provided with a plug that includes an elastic body such as a rubber type material, or the specimen injecting section is covered by resin such as polydimethylsiloxane (PDMS) or by a reinforced film, for preventing leakage to the outside, infection and pollution and for securing tight sealing.

For example, the specimen in syringe is injected by a needle pierced through the plug made of rubber material, or through a needle through which a thin hole having a cap penetrates.

In the case of the former, it is preferable, that, when the needle is pulled out, the hole made by the needle is closed immediately.

Or, another specimen injecting mechanism may also be provided.

The specimen injected in a specimen storage section (not shown) is subjected to preprocessing through mixing of the specimen and the processing liquid, for example, before mixing with reagent 58, as occasion demands, in the specimen preprocessing section provided on the reagent storage section 60 in advance.

Preferable specimen preprocessing includes separation, or concentration and deproteinization of an analysis object (analite).

Therefore, a specimen preprocessing section may include a separation filter, resin for adsorption and beads.

Further, in reagent supply hole 56 of the testing chip 50, there is sealed predetermined amount of necessary reagent in advance.

Accordingly, it is not necessary to fill necessary amount of reagent 58 each time of using, the chip 50 being ready to use at any time.

When analyzing bio-materials in the specimen, respective reagents which are necessary for measurement are usually known.

For example, when analyzing an antigen existing in bio-materials, there is used reagent 58 containing an antibody corresponding to the antigen, preferably containing monoclonal antibody.

The antibody is preferably marked with biotin and FITC.

Reagents for genetic test may include various reagents used for gene amplification, probes used for detection and color forming reagents, and even preprocessing reagents used for specimen preprocessing, as occasion demands.

Reagent 58 is forced out to mixing section 70 from each reagent storage section 60 when driving liquid 31 is supplied into the testing chip 50 by a micro-pump 21 of micro-pump unit 26.

Further, when these reagents 58 are pushed into micro flow channel 46 to be merged with specimens at the downstream side of the micro flow channel 46, there is started reaction necessary for analyses, such as gene amplification reaction, trapping of an analite or antigen-antibody reaction.

With respect to mixing of reagent 58 and reagent 58, and mixing of a specimen and reagent 58, the mixing may be conducted at a desired ratio at a single mixing section, or the mixing may be conducted by providing plural merging points and dividing either one or both of them which are to be mixed such that a desired mixing ratio is be obtained finally.

An embodiment of the reaction region of this kind is not limited in particular, and various embodiments and styles are considered.

As an example, micro flow channel 46 where respective types of liquids are diffused and mixed is provided after a merging point (channel diverging point) where two or more kinds of liquids including reagent 58 are merged, and reactions are carried out in a liquid reservoir (not shown) formed by a space whose width is greater than that of micro flow channel 46 and which is provided after the downstream side of the aforesaid micro flow channel 46.

As a DNA amplification method, a PCR amplification method which is used commonly in many aspects can be used.

Various conditions for practicing the amplification technology are studied in detail, and they are described in various documents including points of improvement.

In the PCR amplification method, it is necessary to control temperatures in three temperatures, and a channel device capable of controlling temperatures suitable for the testing chip 50 has already been proposed by the inventors of the present invention (TOKUKAI No. 2004-108285).

This device system may be applied to a channel for amplification of the testing chip 50 of the invention.

Thus, DNA amplification can be carried out in a period that is much shorter than that for the conventional method wherein DNA amplification is carried out manually, because thermal cycle can be switched at high speed, and micro flow channel 46 is made to be a micro-reaction cell whose heat capacity is small.

ICAN (Isothermal chimera primer initiated nucleic acid amplification) developed recently as an improvement of PCR is characterized in that DNA amplification can be carried out in a short period of time under an optional certain temperature in a range of 50-65° C. (U.S. Pat. No. 3,433,929).

Therefore, the ICAN method is a suitable amplification technology for the testing chip 50 of the invention, because temperature control is simple.

This method which takes one hour in the manual operations is completed in 10-20 minutes, preferably in 15 minutes including also analyses, in the micro-overall-analysis system of the invention.

In the downstream side of the reaction region in the micro flow channel 46 of the testing chip 50, there is provided an analite, for example, a detection region for detecting an amplified gene.

At least its detecting portion is of the transparent material for making optical measurement possible, and preferably of transparent plastic.

Further, protein having affinity to biotin adsorbed to the detection region on the micro flow channel 46 (avidin, strepto avidin, extra-avidin (R), preferably strepto avidin) combines specifically with biotin marked on probe substance; or biotin marked on 5' end of primer used for gene amplification reaction:

Due to this, a probe marked with biotin or amplified gene is trapped at the detection region.

Though a method for detecting separated analite or DNA of amplified target gene is not limited in particular, the following process is basically carried out as a preferred embodiment.

Namely, (1a) cDNA compounded based on specimen or DNA extracted from the specimen, or based-on specimen or RNA extracted from the specimen through reverse transfer and primer biotin-modified at 5' position are sent from their storage sections to a micro flow channel located at the down stream side.

After the process to amplify a gene in a micro flow channel of a reaction region, amplification reaction liquid containing gene amplified in the micro flow channel and a denatured liquid are mixed to make the amplified gene to be a single strand, and this and probe DNA of which end is marked with fluorescence through FITC (fluorescein isothiocyanate) are hybridized.

Then, a liquid is sent to the detection region in the micro flow channel where protein having affinity to biotin is adsorbed, and the amplified gene is trapped in the detection region in the micro flow channel. (Probe DNA marked with fluorescence may be hybridized after the amplified gene is trapped in the detection region.) (1b) A reagent containing antibody specific for the analite such as an antigen, a metabolite and hormone existing in a specimen, preferably monoclonal antibody, is mixed with a specimen.

In this case, the antibody is marked with biotin and FITC.

Therefore, a product obtained through an antigen-antibody reaction has therein biotin and FITC.

This product is sent to a detection region, in the micro flow channel, which has adsorbed biotin-affinity protein (preferably, streptoavidin) to be fixed on the detection region through the combination of the biotin-affinity protein and the biotin. (2) A gold-colloidal liquid whose surface is modified with anti-FITC antibody that combines specifically with FITC is let to flow into the micro flow channel, and thereby, the gold colloid is adsorbed by FITC modified probe hybridized with fixed analite antibody reactant FITC, or with a gene.

(3) The concentration of the gold colloid in the micro flow channel is measured optically.

<System Main Body>

As shown in FIG. 1, on a front side portion of base main body 12, there are provided testing chip gateway 14 through which testing chip 50 is taken into the inside and display section 18 on which the results of the prescribed tests conducted in the base main body 12 are outputted.

Testing chip 50 is placed on chip conveyance tray 22 which is a mounting section, and then, is taken into the base main body 12 through the testing chip gateway 14, to be mounted therein.

Inside the base main body 12, there are provided various devices to control liquid feeding, reaction and detection in the testing chip 50 placed on the chip conveyance tray 22 as shown in FIG. 2.

In the present example, there are provided micro-pump unit 26 that is connected to pump-connecting section 64 of the testing chip 50 and moves a specimen and a processing liquid to prescribed places and pump-control device 28 that controls liquid feeding of the micro-pump unit 26.

There is further provided temperature control device 38 that includes Peltier element 34 that is in contact with testing chip 50 and controls temperature of reagent, especially controls temperature in a channel of the reaction portion, and of heater 36.

In addition, there is provided detection device 44 that includes LED 40 that emits light for detecting substances to be detected existing in a detection section channel of the testing chip 50 and photodiode 42 that receives transmitted light.

For the system main body of the micro-overall-analysis system 10, there are integrated, on the base main body 12, micro-pump unit 26, pump control device 28 that controls the micro-pump 21, temperature control device 38 that controls temperatures and detecting device 44.

When mounting, on the system main body, the testing chip 50 after injecting a specimen in a specimen storage section (not shown) of the testing chip 50 in which reagent 58 is sealed in advance, mechanical connection for operating the micro-pump 21 for liquid feeding is completed.

Therefore, if the testing chip 50 is mounted on the system main body, reagent storage section 60 of the testing chip 50 becomes ready to operate.

After the analyses are started, liquid feeding for specimens and reagents, gene amplification based on mixing, reaction of combination of an analite and a probe, detection of reactants and optical measurements are carried out automatically as a series of successive processes, and necessary data are stored in a file together with necessary conditions and recorded items, thus, measurement of bio materials is automatically carried out.

Control systems relating to respective controls for liquid feeding, temperatures and reactions and units which are in charge of optical detection, data collection and data processing constitute the system main body, together with a micro-pump 21 and an optical device.

This system main body can be used commonly for respective specimen samples when the testing chip 50 is mounted thereon.

Reaction of gene amplification and its detection are incorporated in a software installed on the system main body as a program together with'control of micro-pump 21 and temperature and with data processing of optical detection, as conditions established in advance concerning an order of liquid feeding, volume and timing.

Detection device 44 that detects reactions in micro flow channel 46 of the testing chip 50 causes, for example, LED to irradiate light for measurement for detection regions on an analysis channel for each test item, and detects transmitted light or reflected light with an optical detection unit such as a photodiode or a photomultiplier tube.

Since every component in the micro-overall-analysis system 10 is downsized to be made handy to carry, the micro-overall-analysis system 10 is not restricted by time and place for its use, and it is excellent in terms of workability and operability.

Further, since measurement can be taken promptly independently of time and place, it is possible to use for emergency medical care and to use personally for home medical care.

It is further possible to use testing chip 50 as a disposable type one, because micro-pump unit 26 used for liquid feeding is incorporated on the system main body side.

On the micro-pump unit 26, there are provided a plurality of micro-pumps 21 corresponding, in terms of a number, to the number of regions to feed liquid by pushing out from the upstream side with driving liquid 31, including, for example, a specimen storage section (not shown), a plurality of reagent supply holes 56, a positive control storage section and a negative control storage section.

In the construction, a micro-pump 21 is connected to testing chip 50 through pump-connecting section 64 of the testing chip 50 to function as a micro-pump 21, when the testing chip 50 is mounted on the system main body.

Namely, on the micro-pump unit 26, there are provided a plurality of micro-pumps 21 and testing chip-connecting section 66 having a channel opening for communicating with the testing chip 50.

Figure 4:
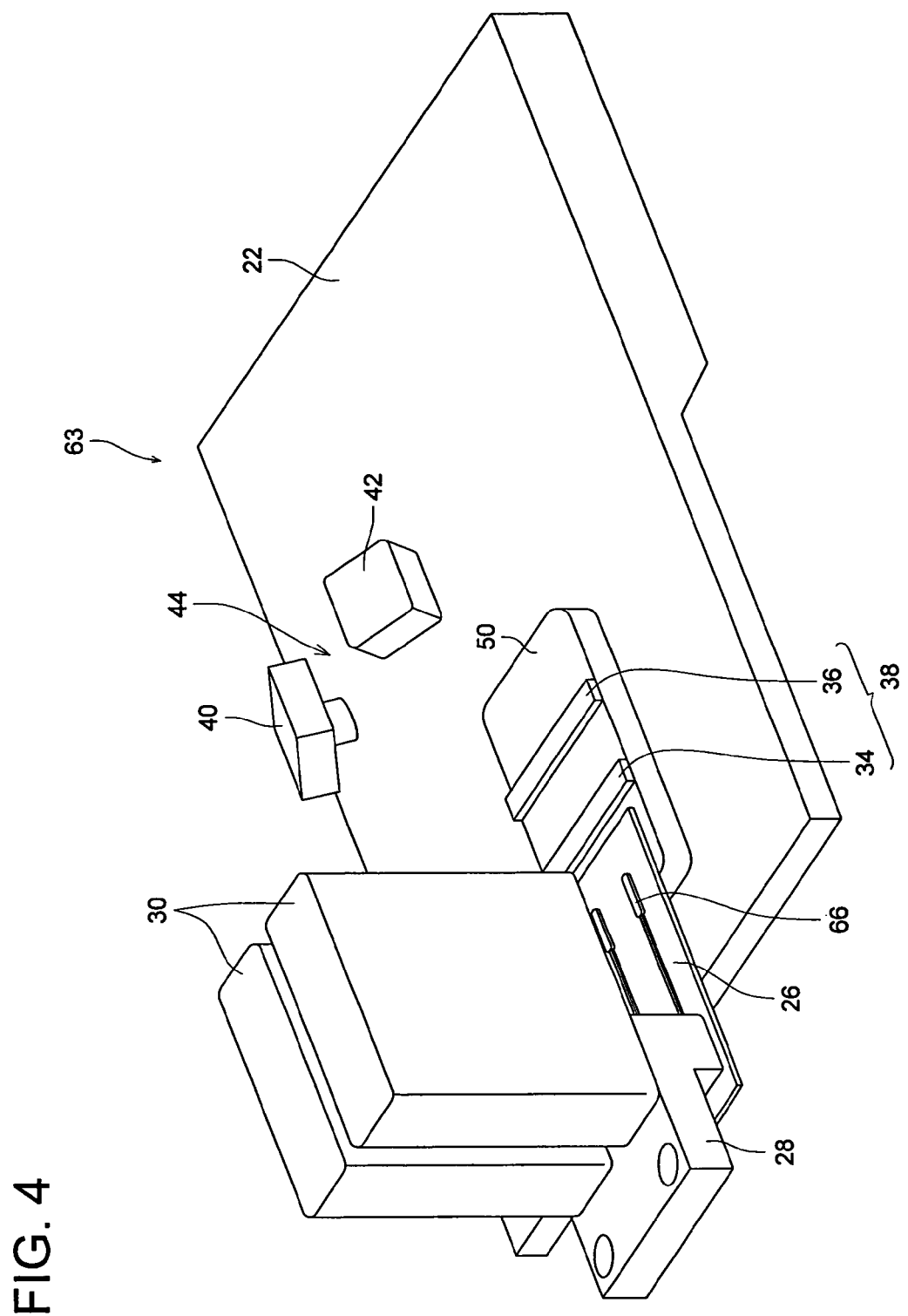
FIG. 4 is a schematic perspective view of a main detection unit shown in FIG. 3.

On the testing chip 50, on the other hand, there is provided pump-connecting section 64 having channel openings for communicating with the micro-pumps 21 as shown in FIG. 4, and the micro-pumps 21 are communicated with reagent storage sections 60 of the testing chip 50, when pump-connecting section 64 of the testing chip 50 is tightly connected to testing chip-connecting section 66 of the micro-pump unit 26 on a liquid-tight basis.

Typically, a pump-connecting section 64 of the testing chip 50 is formed by a channel opening for communicating with the micro-pump 21 and a contact surface surrounding the channel opening, and a testing chip-connecting section 66 is formed by a channel opening for communicating with the micro-pump 21 and a contact surface surrounding the channel opening.

Further, on the upstream side of the pump unit 26, there are provided pump control device 28 that controls driving of the micro-pump 21 and driving liquid reservoir tank 30 that stores driving liquid 31.

By making the contact surface of the micro-pump unit 26 side and the contact surface of the testing chip 50 side tightly contact with each other such that the channel opening on the testing chip 50 side and the channel opening on the micro-pump unit 26 side fit with each other, the aforesaid openings are connected with each other.

Tight contact is attained by pressing testing chip 50, for example, against micro-pump unit 26.

As a micro-pump 21, it is preferable to use a piezoelectric pump.

This piezoelectric pump is a pump which is equipped with a first channel whose channel resistance varies depending on a differential pressure, a second channel whose change rate of channel resistance for the change of differential pressure is smaller than that of the first channel, a compression chamber that is connected to the first and second channels and an actuator that changes inner pressure of the compression chamber, and is capable of feeding a liquid both in a regular direction and an opposite direction, by driving the actuator.

Its details are described in the aforesaid Patent Document 7 and Patent Document 8.

In the aforesaid piezoelectric pump, it is possible to control the liquid feeding direction and the liquid feeding speed by changing the driving voltage and the frequency of the pump.

As an example, a silicon wafer is processed into a predetermined form by a known photolithography technology to produce a silicon substrate. The silicon substrate is formed into the form of the pump through etching. Then, another substrate is superimposed thereon. Thus, a piezoelectric pump is produced.

It is possible to make a pump unit wherein a number of piezoelectric pumps are provided on a sheet of silicone substrate, by the photolithography technology.

For example, a port is formed on the substrate of the pump unit, so that a pump is communicated with pump-connecting section 64 of the testing chip 50 through this port.

By superimposing the vicinity of pump-connecting section 64 of the testing chip 50 vertically on the substrate on which the port is formed, the testing chip 50 can be connected to the pump unit.

Further, the driving liquid reservoir tank 30 is connected to a port of the pump on the opposite side to the port connected with the testing chip 50. When there is a plurality of micro-pumps 21, plural ports provided respectively for these pumps may also be connected to the common driving liquid reservoir tank 30.

FIG. 4 shows main detection unit 63.

In the main detection unit 63, driving liquid 31 is supplied to pump unit 26 from the driving liquid reservoir tank 30 in accordance with instruction signals from pump control device 28, then, the driving liquid 31 is supplied from the micro-pump 21 of the pump unit 26 to the testing chip 50 side through channel 59 (final flow channel) and testing chip-connecting section 66 provided at the downstream side (refer to FIG. 5), to be supplied to a specimen storage section (not shown) or to reagent storage section 60.

After that, a specimen in the specimen storage section and a reagent in the reagent storage section 60 are merged and mixed through a Y-shaped channel, to be raised to a predetermined temperatures by temperature control device 38 in channel 46 so that reactions are promoted, whereby, the reactions are detected.

An analysis system of the invention can be used favorably especially for a test of a gene or a nucleic acid. In this case, a micro flow channel of testing chip 50 is structured to be suitable for PCR amplification. However, as for the basic structure of the channel, it is substantially the same even for bio-materials other than genes.

Various types of reagents used for gene amplification, probes used for detection and color reagents are included in reagents for gene testing, and preprocessing reagent may also be included in the reagents for testing of genes if necessary.

Mixing between reagents and mixing between a specimen and a reagent may be carried out on a single merging point at a desired mixing ratio, or mixing may be carried out by providing plural merging points and dividing either one of them which are to be mixed or dividing both of them so that a desired mixing ratio is obtained finally. An embodiment of reaction regions is not limited in particular, and various embodiments and types are considered, not to be limited to FIG. 2.

In any case, in micro-overall-analysis system 10, when testing chip 50 is fitted in specimen analyzer 2, micro-pump-connecting section 64 on the testing chip 50 side needs to be connected closely to testing chip-connecting section 66 on the specimen analyzer 2 side so that liquid channels and the like are communicated.

Such a tight contact can be achieved by providing, for example, a pressing mechanism between micro-pump unit 26 and testing chip 50.

As the pressing mechanism, there are considered various embodiments, depending on how to fit the testing chip 50 in specimen analyzer 2. Incidentally, in FIG. 1, the specimen analyzer 2 is provided with conveyance tray 22 on which the testing chip 50 is placed. However, this conveyance tray 22 is not essential naturally, and this pressing mechanism can be applied also to a specimen analyzer 2 which is not provided with conveyance tray 22, as described later.

In this case, a wind-powered apparatus, a suction unit and an electromagnet can be used as the pressing mechanism. Further, the pressing mechanism can be provided on pump unit 26, detection device 44, temperature control device 38 or conveyance tray 22.

Figure 6:
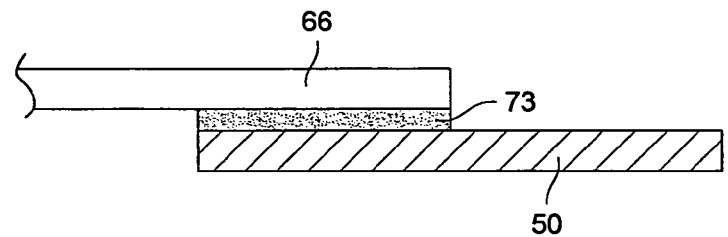
FIG. 6 is a cross-sectional view in the case of using sealing material, as an example of a pressing mechanism provided relating to the main detection unit shown in FIG. 3.

For example, when setting the testing chip conveyance tray 22, shown in FIG. 1, at a predetermined position by inserting the tray 22 into the inside from entrance 14 of base main body (apparatus main body) 12 and by conveying it to primary detection unit 63 in the base main body 12, it is possible to arrange the pressing mechanism by pressing slightly upward from the lower portion or downward from the upper portion, with a proper means, for example, with a cylinder, at a point of time when the conveyance tray 22 arrives at the prescribed position on the primary detection unit 63. A wind-powered apparatus or a suction unit may also be used for the pressing mechanism. It is further possible to provide the pressing mechanism at a position between pump unit 26 and testing chip conveyance tray 22 on which testing chip 50 is placed. When a different member is made to come in contact with a surface of the testing chip 50, it is preferable to use an elastic object of a felt so that neither damage nor defectiveness may be caused. When arranging a pressing mechanism between the pump unit 26 and testing chip conveyance tray 22, it is possible to interpose sealing member 73 deformable by compression between both connection surfaces as shown in FIG. 6. It is preferable that the sealing member 73 of this kind is attached in advance on the connection surface on the side of testing chip connecting section 66 to be replaceable. Though the pressing mechanism of this kind is generally constructed by making use of pump unit 26, it is also possible to use temperature control device 38 or detection device 44, depending on arrangement of members or on surrounding structures.

Incidentally, the temperature control device 38 includes Peltier element 34 that establishes a temperature of a reagent held in reagent storage section 60 in advance to be a predetermined temperature or lower and heater 36 that conducts heating for accelerating reaction of mixed liquid for testing and reagent in micro flow channel 46. If these Peltier element 34 and heater 36 are surely brought into close contact with testing chip 50, quality of the reagent can be maintained at, good conditions for a long time, and results of detections can be obtained promptly by accelerating reactions, after the reagent and the specimen are merged together.

Figure 7:
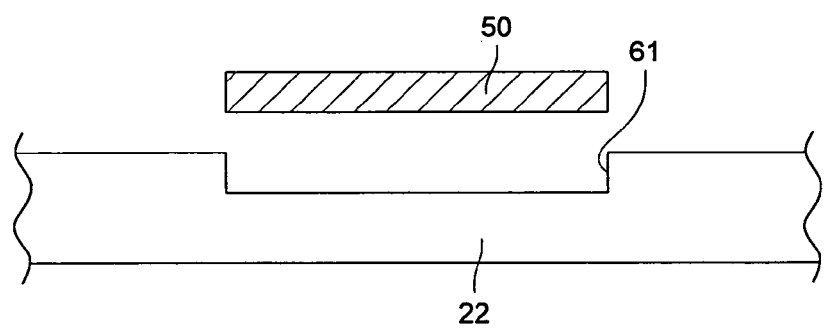
FIG. 7 is an illustration showing an example of a positioning unit equipped on the pressing mechanism of the micro-overall-analysis system of the invention.
Figure 8:
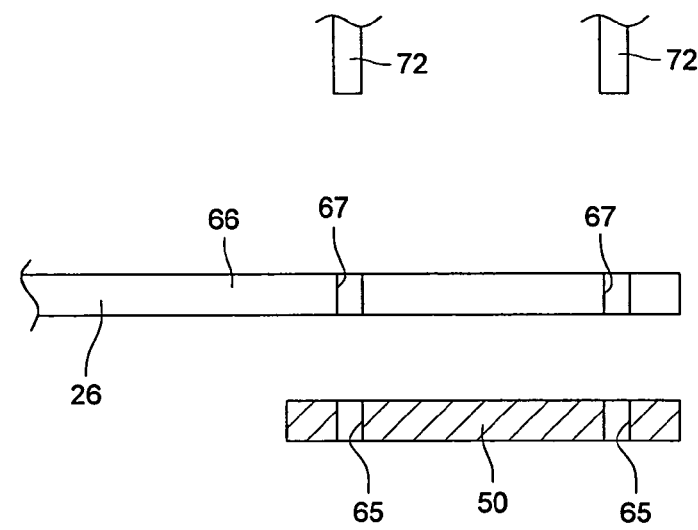
FIG. 8 is an illustration showing another example of a positioning unit equipped on the pressing mechanism of the micro-overall-analysis system of the invention.

It is further preferable that the pressing mechanism is equipped with a positioning A positioning unit may also be one for which groove 61 is formed on conveyance tray 22 and testing chip 50 is guided to a prescribed position along the groove 61, as shown in FIG. 7. Or, it may also be one for which at least two holes 67 are formed on testing chip connecting section 66 of pump unit 26, and holes 65 corresponding to the holes 67 are formed on chip 1, then, holes 67 are made to fit with holes 65 by a sensor, and pins 72 or projections are inserted downward into these holes, as shown in FIG. 8.

Figure 9:
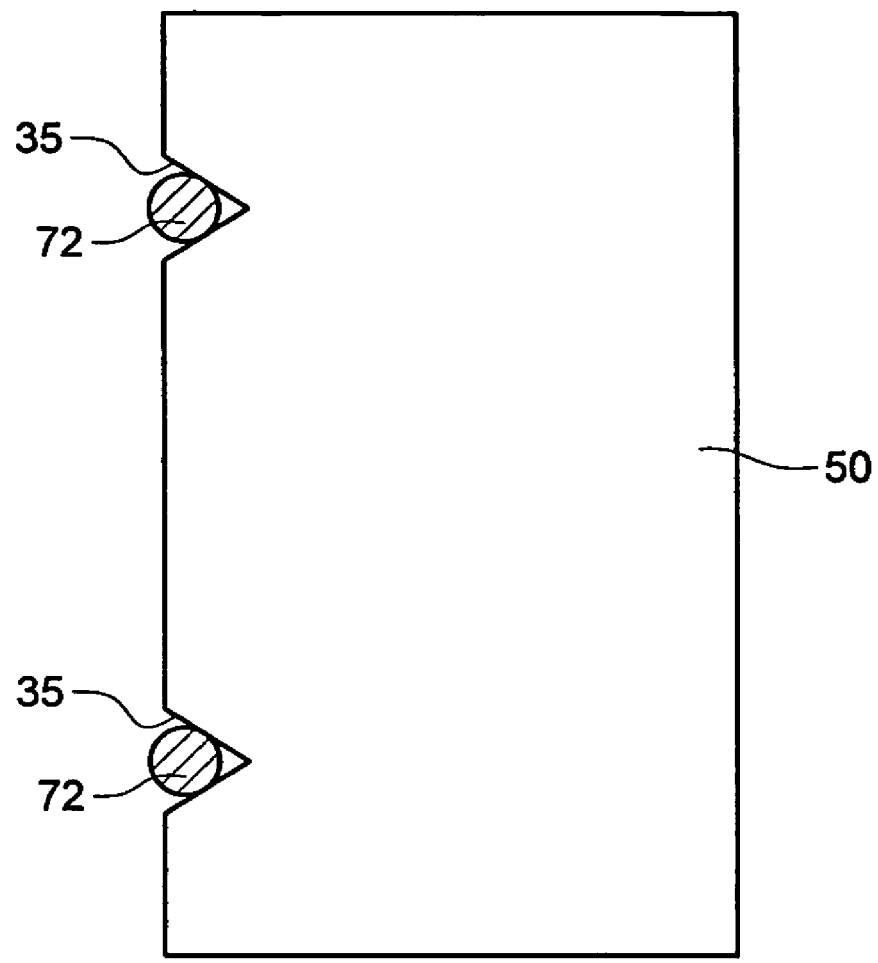
FIG. 9 is an illustration showing still another example of a positioning unit equipped on the pressing mechanism of the micro-overall-analysis system of the invention.

It is further possible to employ a structure for which notches 35 are formed on the side of the testing chip 50, and projections 72 are made to fit with the notches 35, as shown in FIG. 9.

Further, if the pressing mechanism interposed at the connecting section between the testing chip 50 and specimen analyzer 2 is applied also to the temperature control device 38, a contact in a proper state can be obtained between the testing chip 50 and Peltier element 34 or between the testing chip 50 and heater 36, which makes it possible to properly control a temperature at a predetermined region such as a reagent storage section or a reaction portion of the testing chip 50.

Various types of embodiments can be considered for the positioning unit, and the invention is not limited to the aforesaid examples.

Further, silica gel can be housed in the inside of specimen analyzer 2 in the invention. If these desiccants are interposed, surroundings can be dried well, which prevents adsorption of dusts in the gas, and contributes to improvement of accuracy in analysis. Further, liquid leakage from the connecting section caused by adhesion of moisture at the connecting section between the testing chip 50 and pump unit 26 (micro-pump connecting section 64 and testing chip connecting section 66) can be prevented.

The present invention is not limited to the aforesaid examples at all.

For example, the invention can be applied also to the occasion where the conveyance tray 22 of this kind is not provided on the specimen analyzer 2, although the conveyance tray 22 is provided on the specimen analyzer 2 in the aforesaid example.

Figure 10:
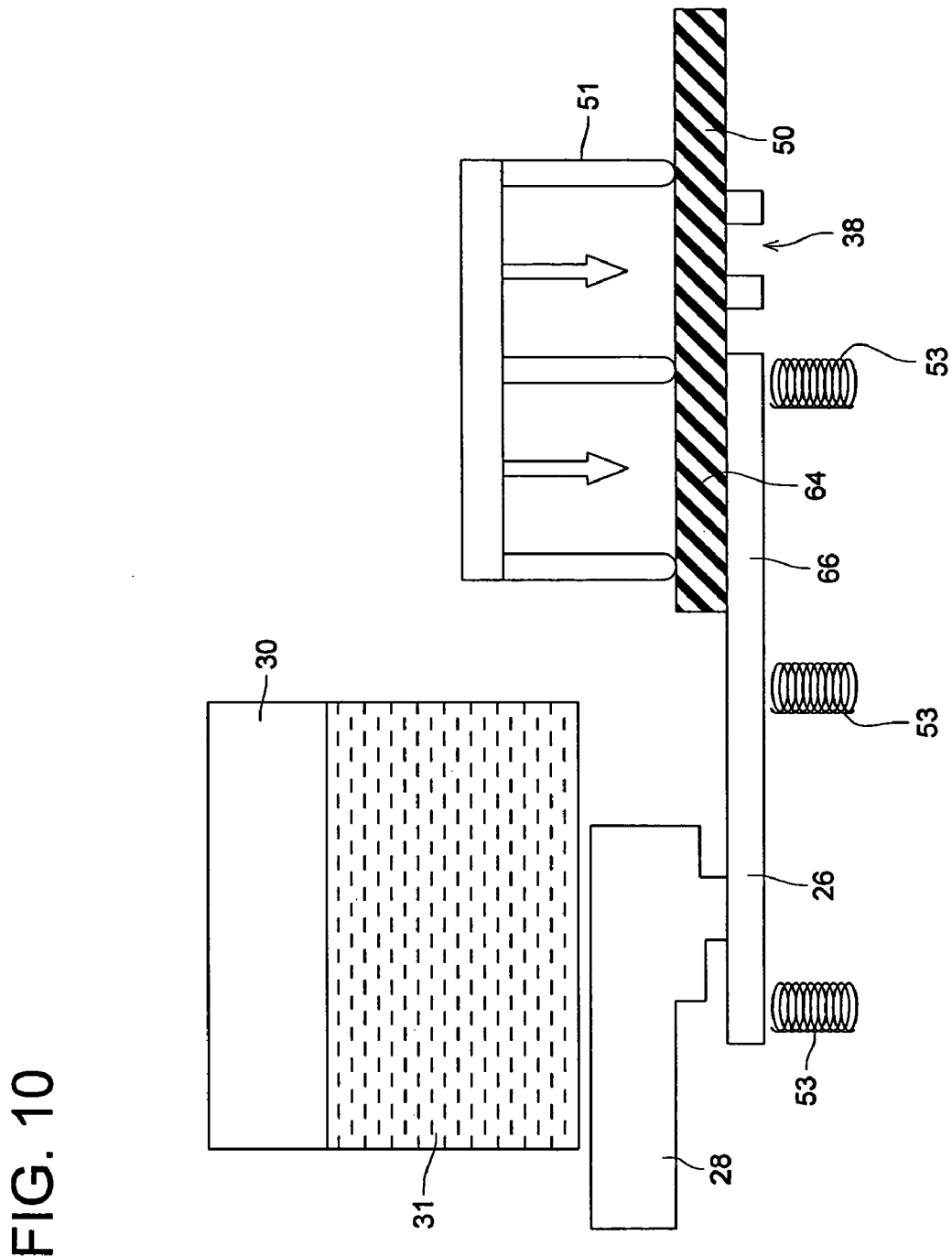
FIG. 10 is a schematic sectional view wherein a testing chip is linked with a pump unit in another example of a micro-overall-analysis system of the invention.
Figure 11:
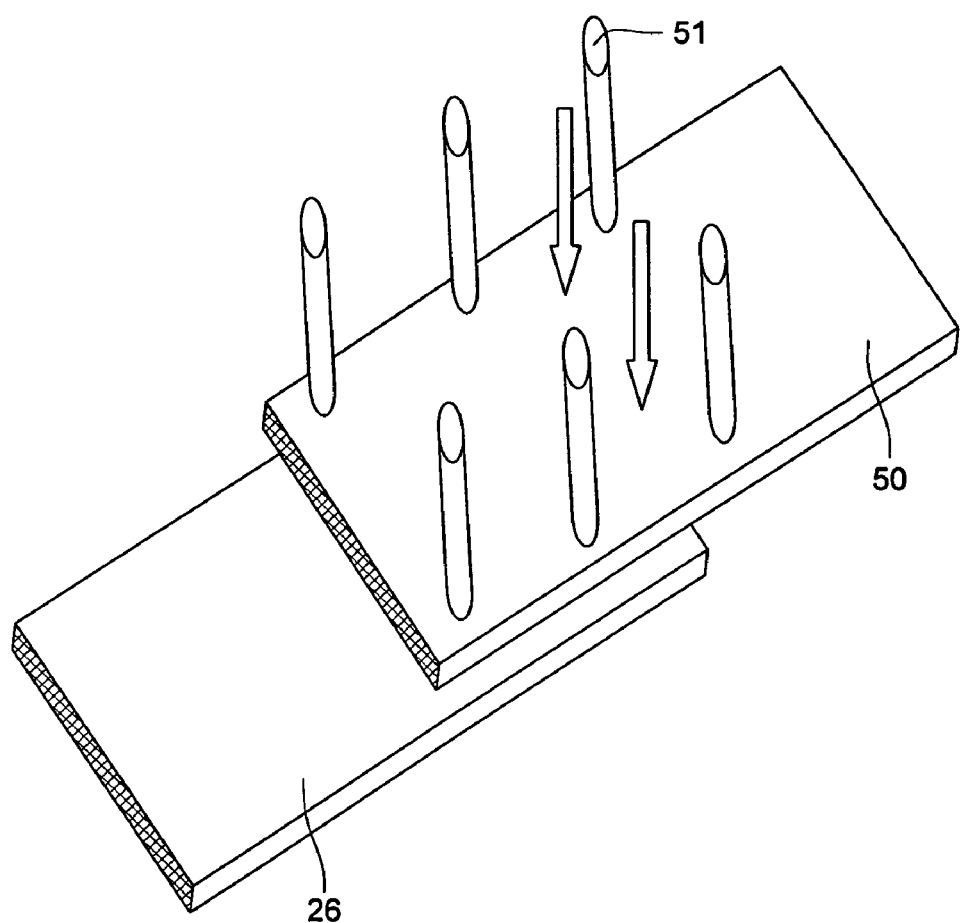
FIG. 11 is a schematic diagram showing operations of a pressing mechanism provided in the other example shown in FIG. 10.

FIG. 10 shows another example of the invention, and in particular, it shows a structure of the inside of the specimen analyzer 2 which is not provided with a conveyance tray 22. Incidentally, in FIG. 10, the same components as those in FIG. 3 are given the same symbols, and detailed description is omitted.

In the present example, micro-pump connecting section 64 is opened on the lower surface of the testing chip 50, and testing chip connecting section 66 is formed to be opened on the upper surface of pump unit 26. The testing chip 50 is arranged on the upper surface of the pump unit 26, with its opening section facing downward.

Meanwhile, in the present example, elastic body 53 such as a spring or a rubber body is interposed below a placing surface of pump unit 26. By interposing the elastic body 53, a relative inclination between testing chip 50 and pump unit 26 can be absorbed, and the tightness of contact between both items is improved accordingly.

Further, in the present example, hydraulic or spring-powered or motor-powered pressing mechanism 51 is provided above the testing chip 50.

Owing to this pressing mechanism 51 thus interposed, the tightness of contact between pump unit 26 and testing chip 50 is improved, which makes it possible to prevent liquid leakage as far as possible.

Figure 12:
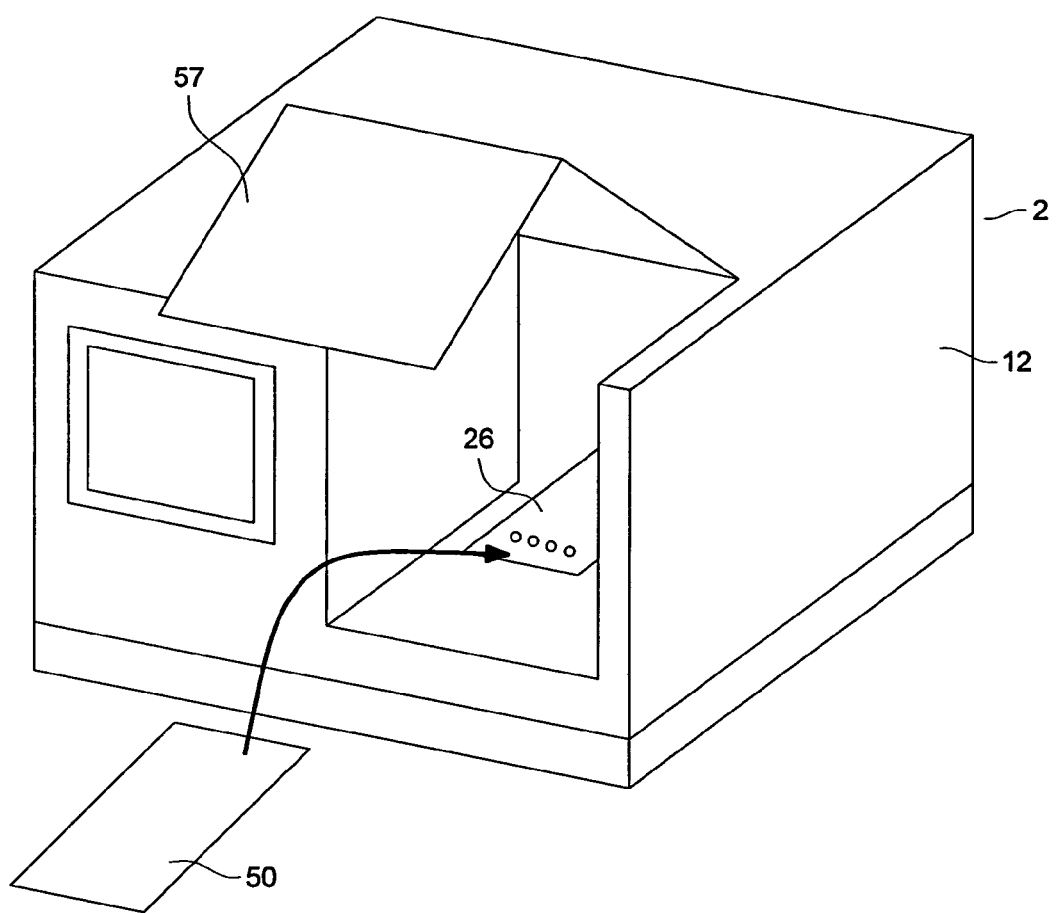
FIG. 12 is a perspective view of a micro-overall-analysis system in another example of the invention.
Figure 13:
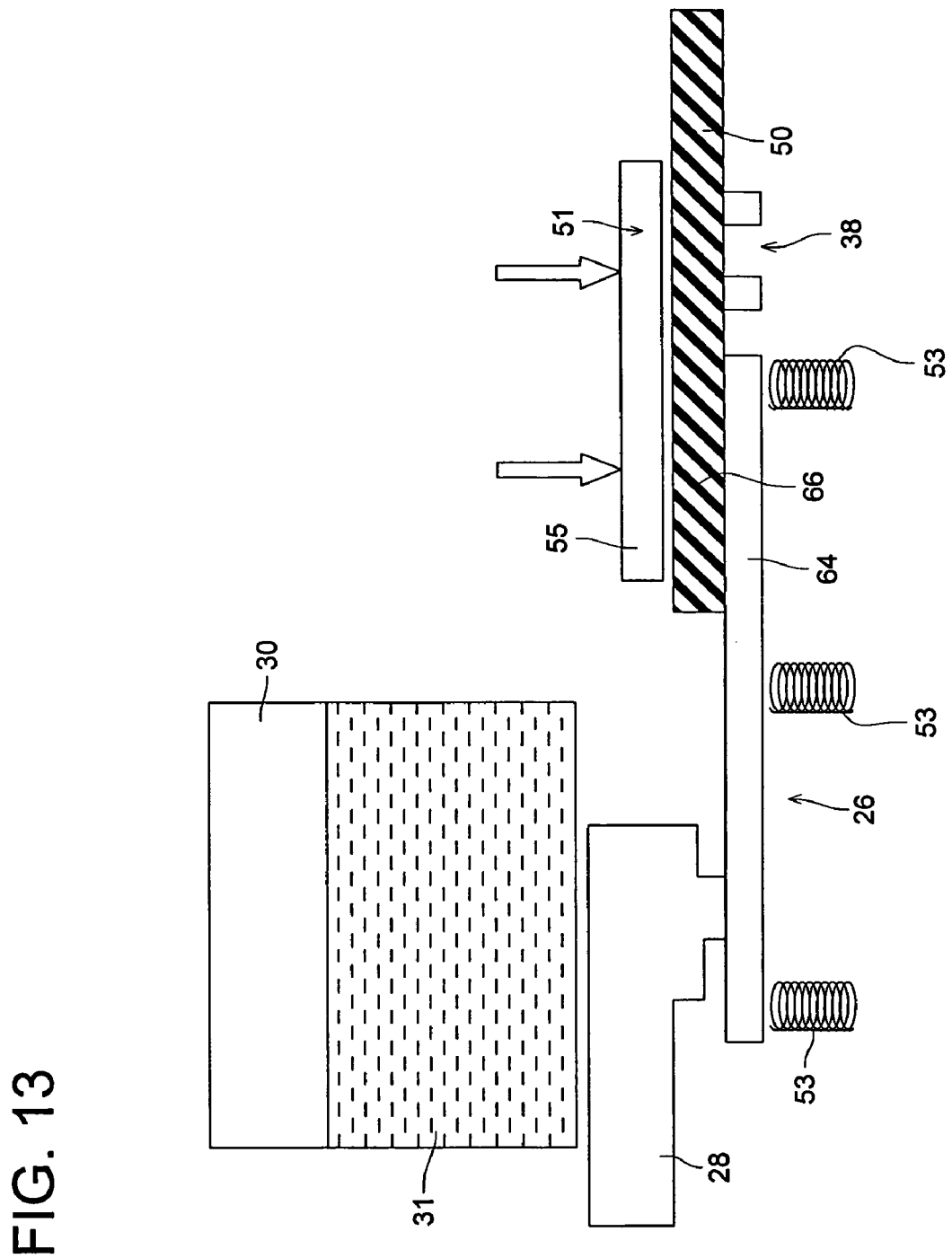
FIG. 13 is a schematic diagram showing the structure of the inside of the specimen analyzer shown in FIG. 12.

Each of FIG. 12 and FIG. 13 shows another example. In this example again, conveyance tray 22 is not provided on the specimen analyzer 2, likewise as in the case of FIG. 10.

On the specimen analyzer 2, there is provided opening and closing door 57 on the front surface of base main body 12, and inside the door 57, there is housed pump unit 26. When testing the testing chip 50, the door 57 is opened first as illustrated, and an operator can place directly the testing chip 50 manually on the pump unit 26 arranged inside. AS the pressing mechanism 51 in this case, plate member 55 capable of moving up and down, for example, can be prepared as a separate member, and hydraulic power, spring force or force of motor can also be applied downward through the plate member 55 representing the separate member. Force of wind may also be employed naturally. If heat insulating materials such as foam polystyrene or Bakelite, for example, is used as the plate member 55, it is possible to test accurately, because a heating temperature and a cooling temperature are stabilized. Even in the case of pressing mechanism 51 of this structure, it is possible to improve the tightness of contact between testing chip 50 and pump unit 26, likewise as in the aforesaid example.

Further, the pressing mechanism relating to the invention may also be conveyance tray 22, temperature control device 38 or pump unit 26; each itself. The pressing mechanism can be constructed by using the gravity force of the aforesaid items.

There has been described the pressing mechanism for preventing liquid leakage from the connecting section that connects micro-pump 21 with testing chip 50, and more preferably, the specimen analyzer 2 is provided with a device to prevent, by removing driving liquid 31 in advance, that a liquid leaks out from the connecting section.

A gas-blower for that purpose will be described as follows.
<Gas-Blower>

In FIG. 3, testing chip 50 inserted into base main body 12 under the condition that the testing chip 50 is placed on the chip conveyance tray 22 is connected with micro-pump unit 26 at pump connecting section 64, at a prescribed position in the base main body 12.

Further, driving liquid 31 such as oil or a buffer liquid stored in driving liquid tank 30 is sent out into the testing chip 50 by a micro-pump 21 that is driven by pump control device 28, and the driving liquid pushes out reagent and others stored in reagent storage section 60 in the testing chip 50 to merging point 70.

In this case, if a surface of testing chip connecting section 66 of the micro-pump unit 26, or a surface of pump connecting section 64 of the testing chip 50 is wet with driving liquid 31, moisture or with other liquids, there is a possibility of a problem that the driving liquid 31 sent from the micro-pump 21 leaks out of the connecting section, even when the micro-pump unit 26 and the testing chip 50 are brought into tight contact with each other.

Therefore, in the present example, gas is sent by gas-blower 32 into channel 20 provided in advance on the testing chip 50, to eliminate driving liquid 31 in advance, at the stage before testing chip connecting section 66 of the connected micro-pump unit 26 is separated from pump connecting section 64 of the testing chip 50, as shown in FIG. 3, thus, leaking out of a liquid from the connecting section is prevented.

The gas-blower 32 of this kind is constructed so that it is connected to gas-blower connecting section 48 provided in advance on the testing chip 50, in the system main body, as shown in FIG. 3.

Figure 14:
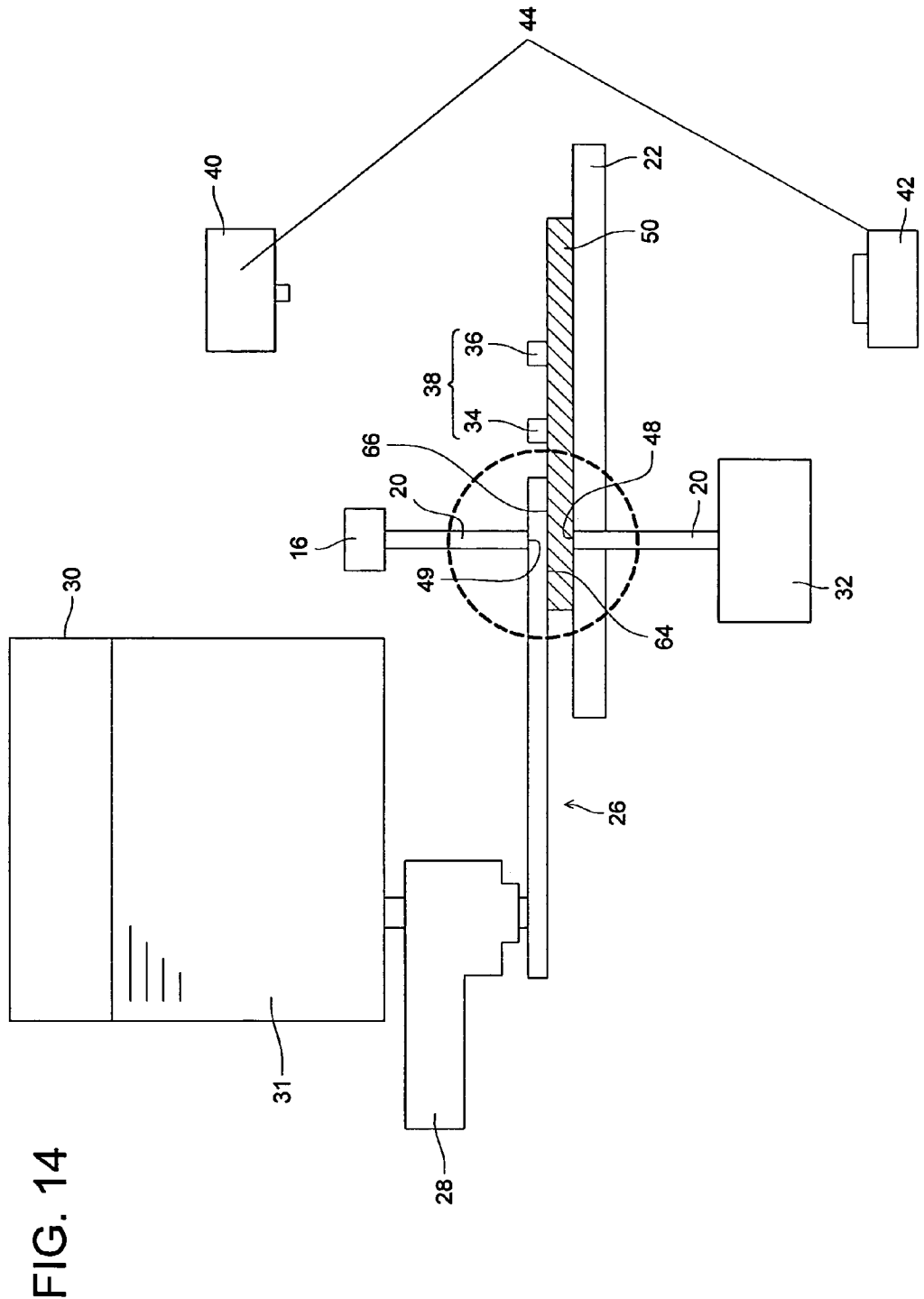
FIG. 14 is another schematic diagram of the inside of a base main body showing how an testing chip is loaded on the base main body of a micro-overall-analysis system in another example.

As another example, on the micro-pump unit 26 connected with pump connecting section 64 of the testing chip 50, there my be provided liquid collection device connecting section 49 as shown in FIG. 14, and liquid collection device 16 is connected to the liquid collection device connecting section 49.

Figure 5:
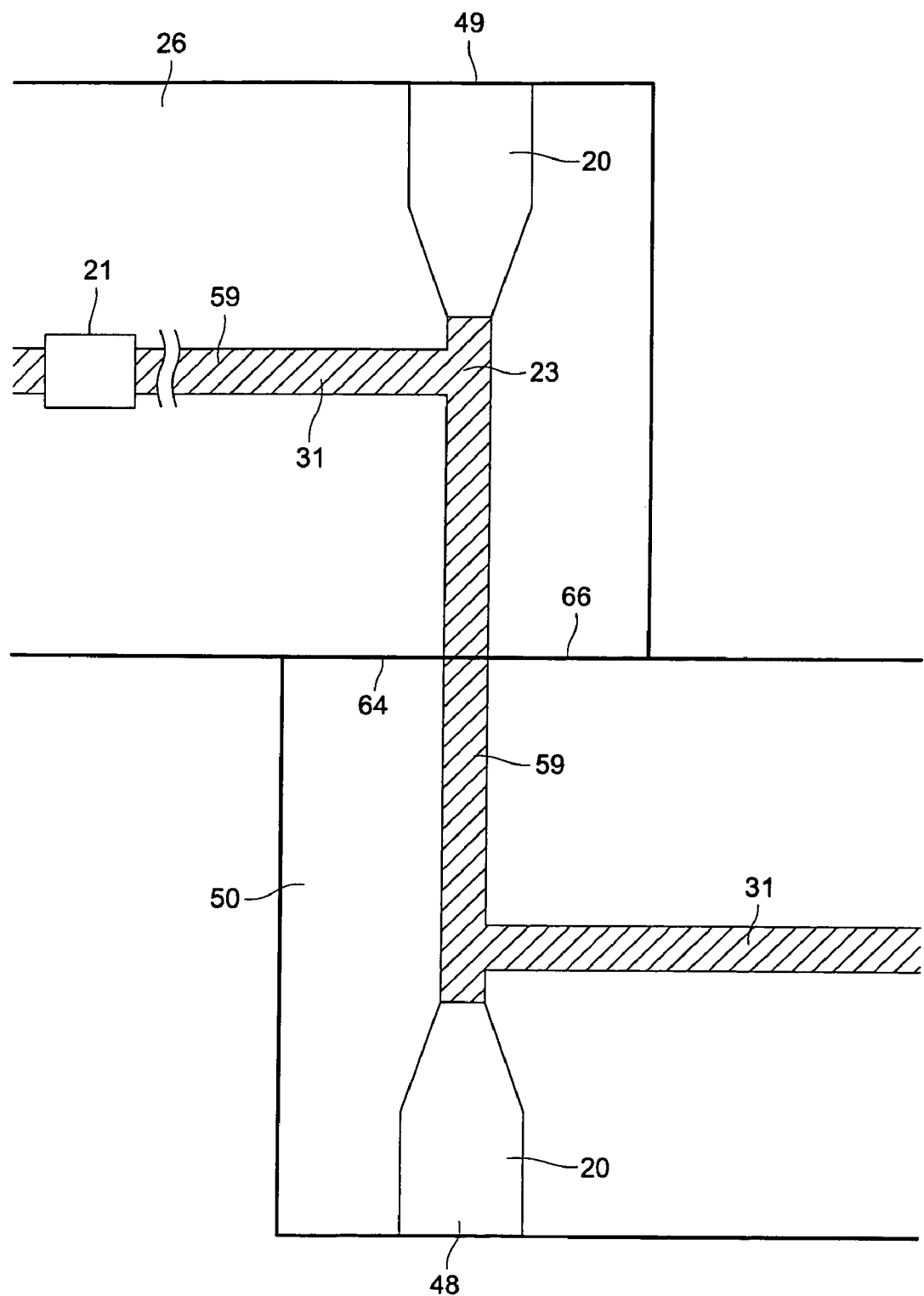
FIG. 5 is an enlarged diagram of a primary portion of the micro-overall-analysis system shown in FIG. 3, wherein the primary portion is enlarged to be shown.

In the liquid collection device 16, gas is taken in channel 20 by the gas-blower 32 in the condition that micro-pump unit 26 is connected to the testing chip 50, as shown in FIG. 5, and further, driving liquid 31 is pushed up to the liquid collection device connecting section 49 of the upper micro-pump unit 26, thus, the driving liquid 31 is collected by the liquid collection device 16 connected to the liquid collection device connecting section 49.

Figure 15:
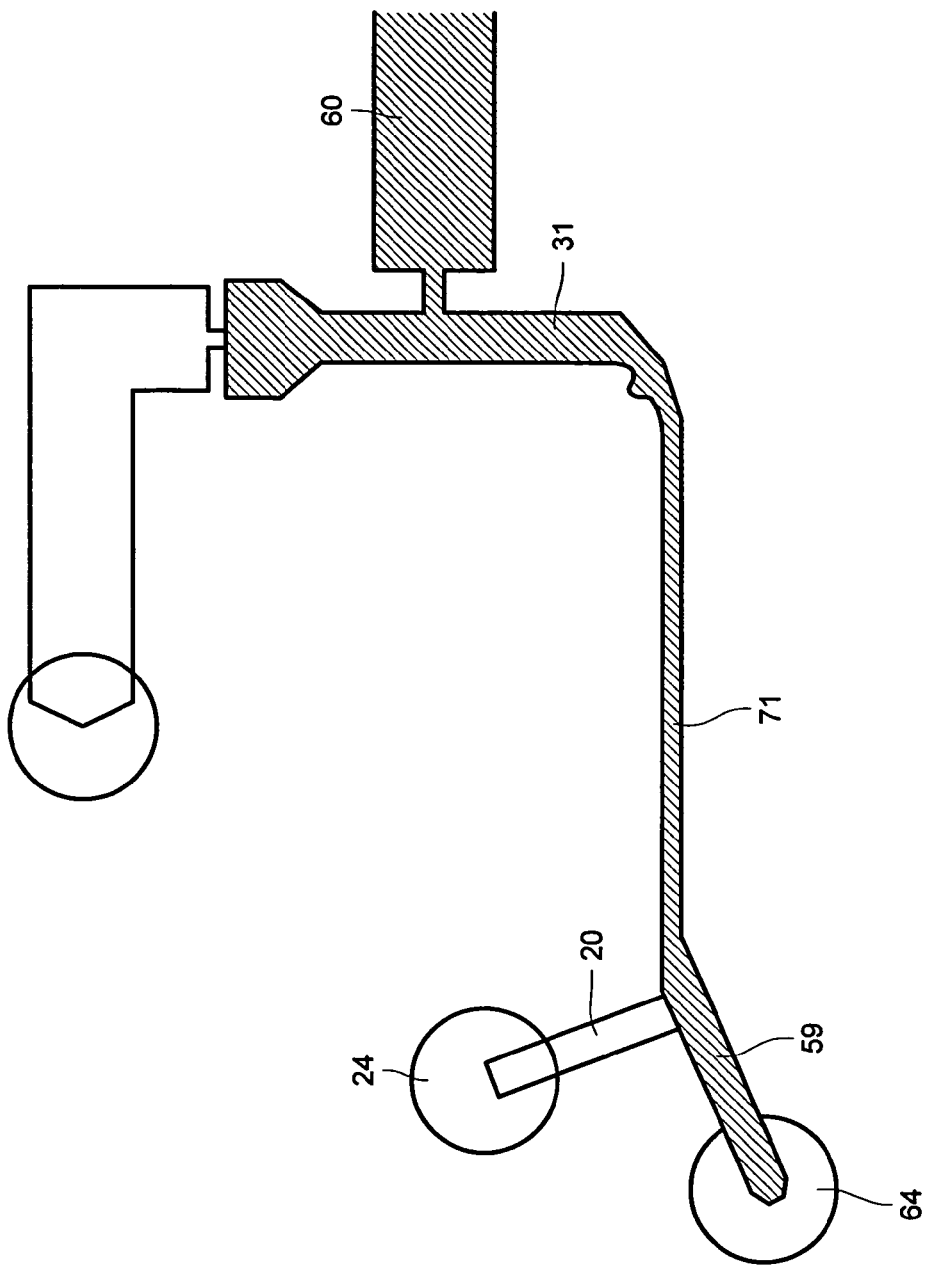
FIG. 15 is an enlarged diagram of a primary portion of the testing chip shown in FIG. 2.

Meanwhile, after gas is taken by the gas-blower 32 into testing chip 50, the gas is surely taken into channel 59 on the pump connecting section 64 side, in the structure, because channel 59 is different from channel 71 in terms of channel diameter, as shown in FIG. 15.

Further, by making a channel on the driving liquid tank 30 side to be different from that on the liquid collection device side in terms of a diameter of the channel, in the same way, even for the micro-pump unit 26 side, driving liquid 31 pushed up by the gas sent out by the gas-blower 32 can surely be collected by the liquid collection device 16, in the structure.

In the flow of collection of driving liquid 31 by the gas-blower 32, the gas-blower 32 is connected to gas-blower connecting section 48 of the testing chip 50, in the condition that testing chip connecting section 66 of micro pump unit 26 is connected to pump connecting section 64 of the testing chip 50 as shown in FIG. 16(a).

If the gas is sent in channel 20 by the gas-blower 32 in such condition, driving liquid 31 filled in channel 59 is pushed upward by gas 68, as shown in FIG. 16 (b).

If the gas is further sent into the channel, driving liquid 31 in channel 59 is moved from the vicinity of the testing chip connecting section 66 and pump connecting section 64 to disappear, as shown in FIG. 16 (c).

If the micro-pump unit 26 is separated from the testing chip 50 in the condition that driving liquid 31 does not exist in the neighborhood of the testing chip connecting section 66 and pump connecting section 64 as this, leakage of a liquid at the connecting section can surely be prevented.

Figure 17:
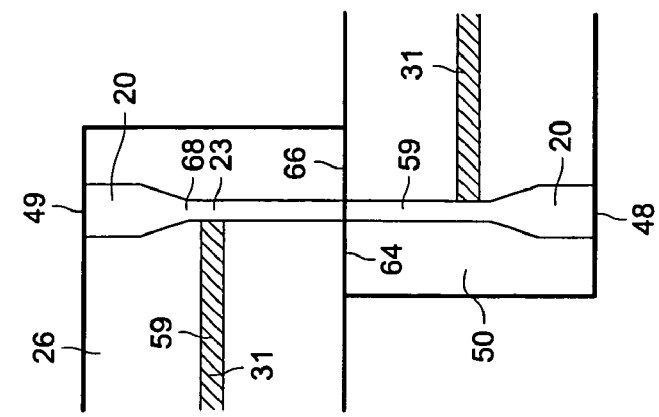
FIGS. 17(a) to 17(c) are schematic diagrams illustrating movement of a liquid in the case of using a gas blower of the micro-overall system of the invention shown in FIG. 14.
Figure 17:
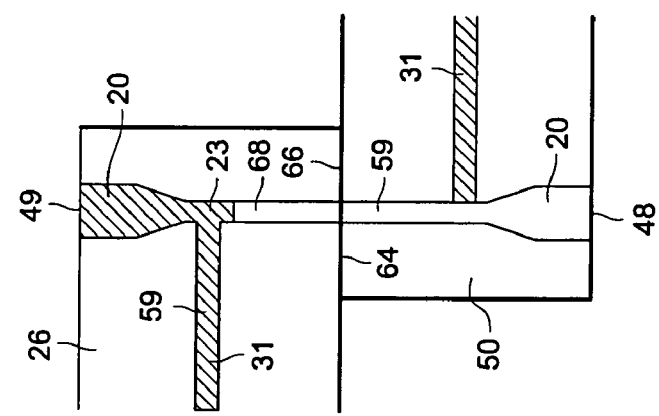
Figure 17:
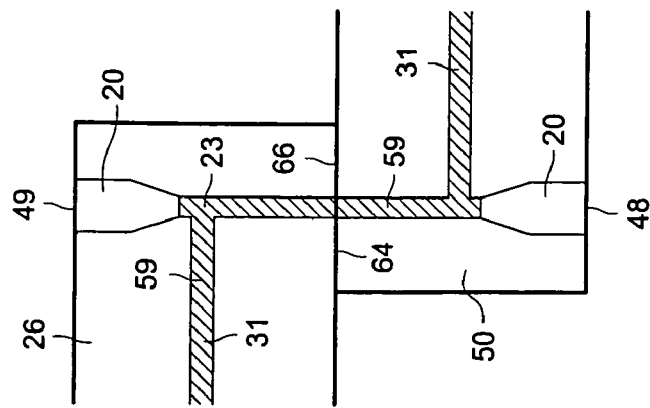

Further, when liquid collection device connecting section 49 is provided on the micro-pump unit 26, the gas-blower 32 is connected to gas-blower connecting section 48 of the testing chip 50, in the condition that testing chip connecting section 66 of micro-pump unit 26 is connected to pump connecting section 64 of the testing chip 50 as shown in FIG. 17 (a).

Further, the liquid collection device 16 is connected to the liquid collection device connecting section 49 of the micro-pump unit 26.

If gas is sent into channel 20 from the gas-blower 32 in the aforesaid condition, driving liquid 31 filled in reagent storage section 60 is pushed upward by gas 68 through connection point 23 between channel 59 (first flow channel) and channel 20 of pump unit 26 (second flow channel) as shown in FIG. 17 (b).

If the gas is further sent into the channel, driving liquid 31 in the reagent storage section 60 is collected in the liquid collection device 16 through the liquid collection device connecting section 49 in the vicinity of the testing chip connecting section 66 and pump connecting section 64 as shown in FIG. 17 (c).

Incidentally, a kind, an amount and a temperature of the gas that is sent out by the gas-blower 32 can be established properly so that they fit with driving liquid 31, a specimen and processing liquid stored in the testing chip 50 and with the structure of the system main body.

The number of gas-blowers 32 can be established properly depending on the number of gas-blower-connecting sections 24 provided in the testing chip.

As an example of the structure establishment, there are given a structure wherein one gas-blower 32 is installed, and this gas-blower 32 is connected to all gas-blower-connecting sections 24 to send gas from a single gas-blower, and a structure wherein a plurality of gas-blowers 32 are installed, and respective gas-blowers 32 are connected with gas-blower-connecting sections 24 on an allotment basis to send the gas.

Further, in the present example, there have been described an occasion in which the gas-blowers 32 is connected to the testing chip 50 side, and driving liquid 31 in the channel near the testing chip connecting section 66 and the pump connecting section 64 is driven out when gas flows in from the testing chip 50 side, and an occasion in which the gas-blowers 32 is connected to the testing chip 50 side, and driving liquid 31 in the channel is collected in the liquid collection device 16 on the micro-pump unit 26, to which, however, the invention is not limited.

For example, it is possible to employ a structure in which the gas-blowers 32 is connected to the micro-pump unit 26 side, and driving liquid 31 in the channel near the testing chip connecting section 66 and the pump connecting section 64 is driven out when gas flows in from the micro-pump unit 26 side, and to employ a structure in which the gas-blowers 32 is connected to the micro-pump unit 26 side, and a liquid is collected by providing the liquid collection device 16 on the testing chip 50 side.

It is further possible to constitute to make the gas-blower to be switched freely so that it may be used on both the micro-pump unit 26 side and the testing chip 50 side, which can be varied within a range that does not depart from the spirit and scope of the invention.

<Hydrophobic Layer>

It is possible to provide a hydrophobic layer on the surface of the testing chip connecting section 66 or the pump connecting section 64.

Conventionally, the micro-pump unit 26 and the testing chip 50 are brought into close contact and driving liquid 31 is made to flow in reagent storage section 60, as shown in FIG. 18 (a-1), and then the micro-pump unit 26 are separated from the testing chip 50, as shown in FIG. 18 (a-2).

In this case, driving liquid 31 on the surface of the pump connecting section 64 and that on the surface of the testing chip connecting section 66 are connected to each other during the initial period of the separation, and a distance between the pump connecting section 64 and the testing chip connecting section 66 is further broadened to cut the connected liquid.

In the case of cutting the connected liquid, the liquid sometimes scatters in the system main body or on the testing chip 50.

In the present example of the invention, hydrophobic layer 52 is provided on the surface of the pump connecting section 64 and that of the testing chip connecting section 66, and in this condition, the micro-pump unit 26 and the testing chip 50 are brought into close contact each other.

When the micro-pump unit 26 is separated from the testing chip 50, surface tension of driving liquid 31 is generated by the hydrophobic layer 52 provided on the surface of the pump connecting section 64 and that of the testing chip connecting section 66, which contributes to smooth cutting of the liquid.

The hydrophobic layer 52 of this kind is just required to be a sealing member made of soft resin such as polyethylene, silicone and Teflon (a registered trademark), for example, and a sealing surface of the sealing member is preferably made to be a contact surface between the testing chip 50 and micro-pump unit 26.

As stated above, in the present example, leakage of liquid from the connecting section is prevented by the pressing mechanism while the micro-pump unit 26 is connected to the testing chip 50, and further, at the stage before the testing chip connecting section 66 of the connected micro-pump unit 26 is separated from the pump connecting section 64 of the testing chip 50, liquid leakage from the connecting section is prevented by sending gas into channel 20 provided, in the testing chip 50 in advance from gas-blower 32 (shown in FIG. 3), and thereby, by removing driving liquid 31 in advance.

Figure 19:
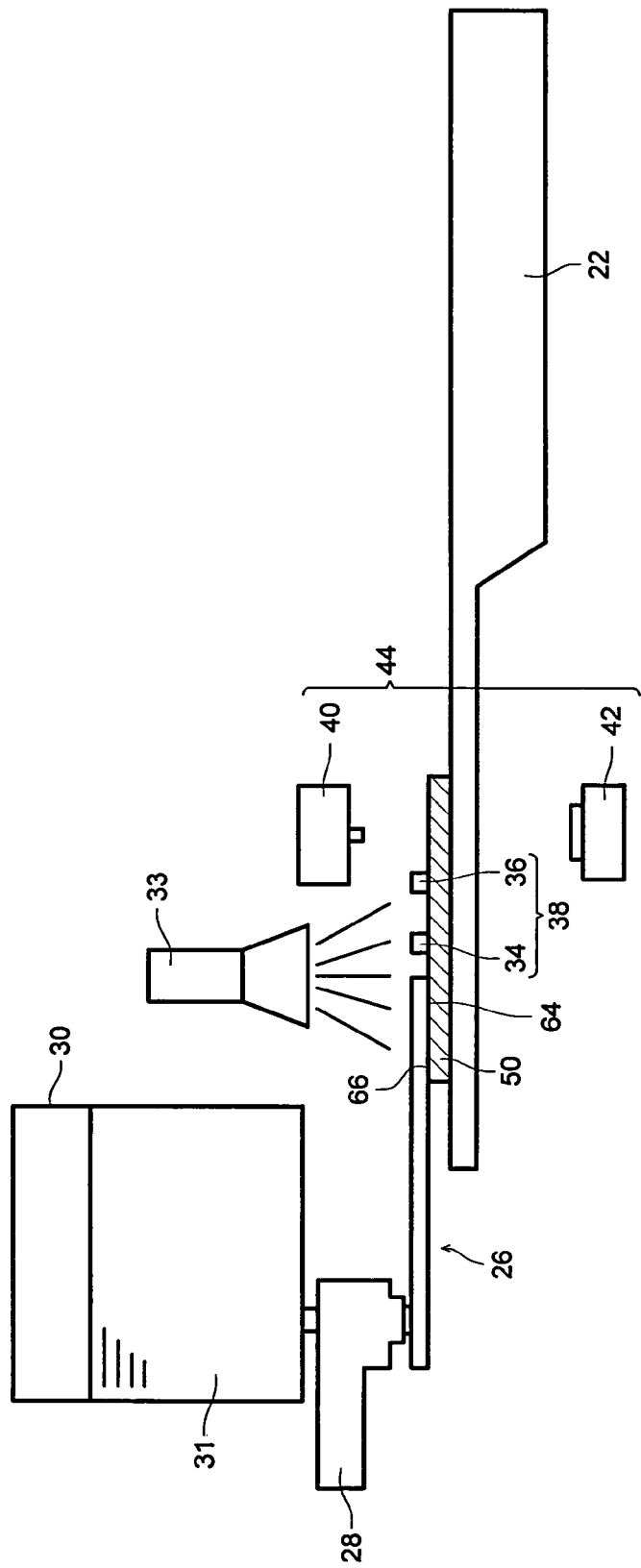
FIG. 19 is a schematic diagram illustrating the circumstance wherein an testing chip is loaded on the base main body of the micro-overall-analysis system in the example shown in FIG. 1 and illustrating a cleaning device.

For preventing the liquid leakage more surely, in the present example, as shown in FIG. 19, gas-blower 33 is provided more preferably, to send a wind to the contact surface in advance with the gas-blower 33 before the micro-pump 21 is connected to the testing chip 50 to clean the contact surface by blowing off (or drying) a liquid on the contact surface. The foregoing is also applied even to the occasion in which the contact surface is contaminated with foreign substances.

Incidentally, the gas-blower 33 is an gas-blower that is different from the aforesaid gas-blower 32; namely, the gas-blower 32 for preventing liquid leakage from the connecting section by sending gas into channel 20 provided in the testing chip 50 in advance from gas-blower 32, and thereby, removing driving liquid 31 in advance.

An amount, a temperature and a direction of the wind that is sent out by the gas-blower 33 can be established properly so that they fit with a specimen held in the testing chip 50, a processing liquid and with the structure of the system main body.

A place of installation and the number for the gas-blower 33 can be established properly depending on the occasion.

For example, the gas-blower 33 can be installed so that gas may be sent to the surface of the testing chip 50 placed on chip conveyance tray 22 on the pump connecting section side, or, the gas-blower 33 can be installed so that gas may be sent to the surface of micro-pump unit 26 on the testing chip connecting section 66 side.

It is also possible to constitute so that gas may be sent to both of the aforesaid surfaces.

<Wiping Device>

Further, in the present example, wiping device 17 that that removes a liquid (for example, moisture or a specimen) sticking to the surface of the testing chip 50 before the micro-pump 21 is connected to the testing chip 50, is provided above testing chip gateway 14 of the base main body 12 for the testing chip 50, as a mechanism for cleaning the contact surface in advance.

Figure 20:
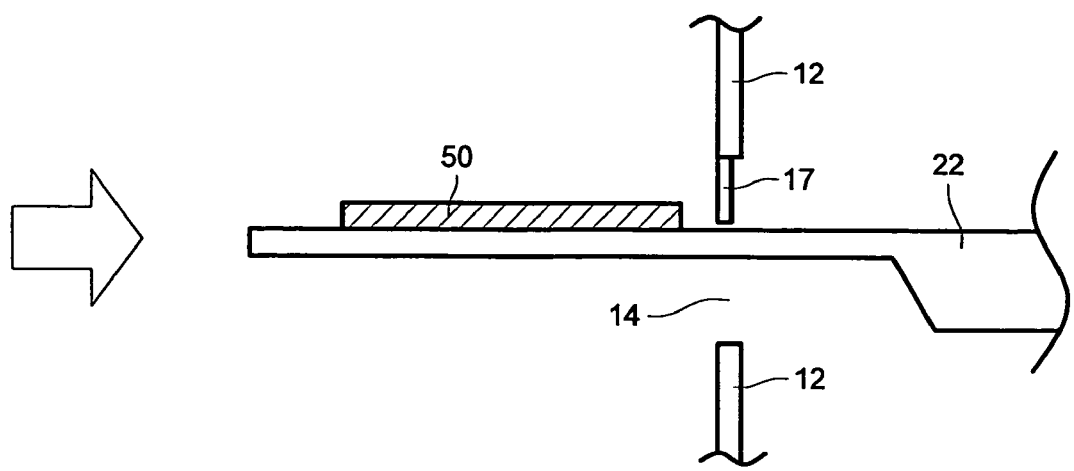
FIGS. 20(a) and 20(b) are partial schematic diagrams illustrating a wiping device of the micro-overall-analysis system of the example in FIG. 1.
Figure 20:
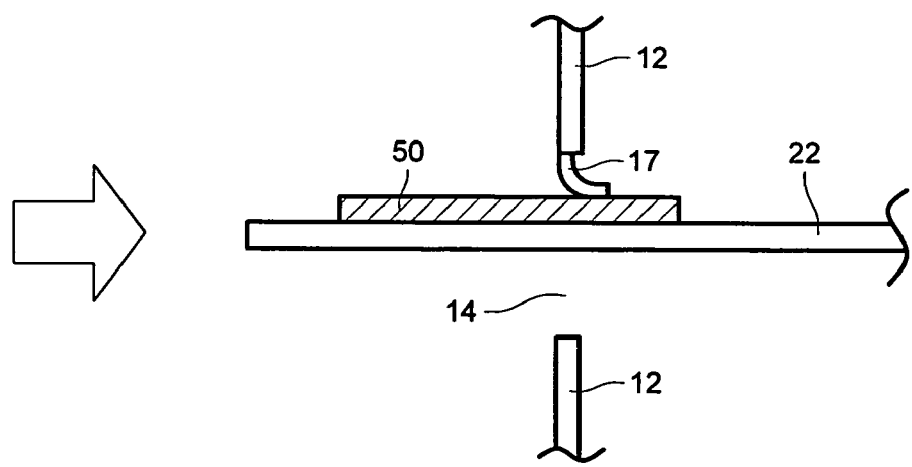

Namely, in the aforesaid structure, when the testing chip 50 is placed on chip conveyance tray 22, and the chip conveyance tray 22 is inserted in the testing chip gateway 14 provided on the front side of the base main body 12 as shown with an arrow in FIG. 20, the chip conveyance tray 22 on which the testing chip 50 is placed is moved in the direction of an arrow shown in FIG. 20 (a), because wiping device 17 is provided above the testing chip gateway 14, and an upper surface of the testing chip 50 comes in contact with the wiping device 17 as shown in FIG. 20 (b), and thereby, liquids and foreign substances sticking to the testing chip 50 are wiped off.

By constituting as stated above, even when a surface of pump connecting section 64 in the testing chip 50 is wet or is contaminated with foreign substances, these substances can be removed by the wiping device 17 before they enter the base main body 12.

Meanwhile, as a wiping material in the wiping device 17 of this kind, there are given scraper-shaped rubber and sponge having excellent water-absorbing property, for example, and it is possible to select those which are appropriate for materials of the testing chip 50.

Though in the present embodiment, testing chip 50 is cleaned, it is also possible to make the wiping device to work on testing chip connecting section 66 to wipe liquids and foreign substances off its surface before connecting the testing chip 50, by providing the wiping device 17 like that stated above on the testing chip connecting section 66 on the micro-pump unit 26.

It is further possible to install both wiping device 17 to clean testing chip 50 and wiping device 17 to clean micro-pump unit 26.

After cleaning is carried out by a cleaning mechanism like that mentioned above, liquid feeding is controlled by a micro-pump 21 and a predetermined test is conducted by using temperature control device 38 and detecting device 44, for the testing chip 50 loaded on the micro-pump unit 26.

Results of the test are displayed on display section 18 provided on the front side of the base main body 12, and the predetermined test is completed.

Figure 21:
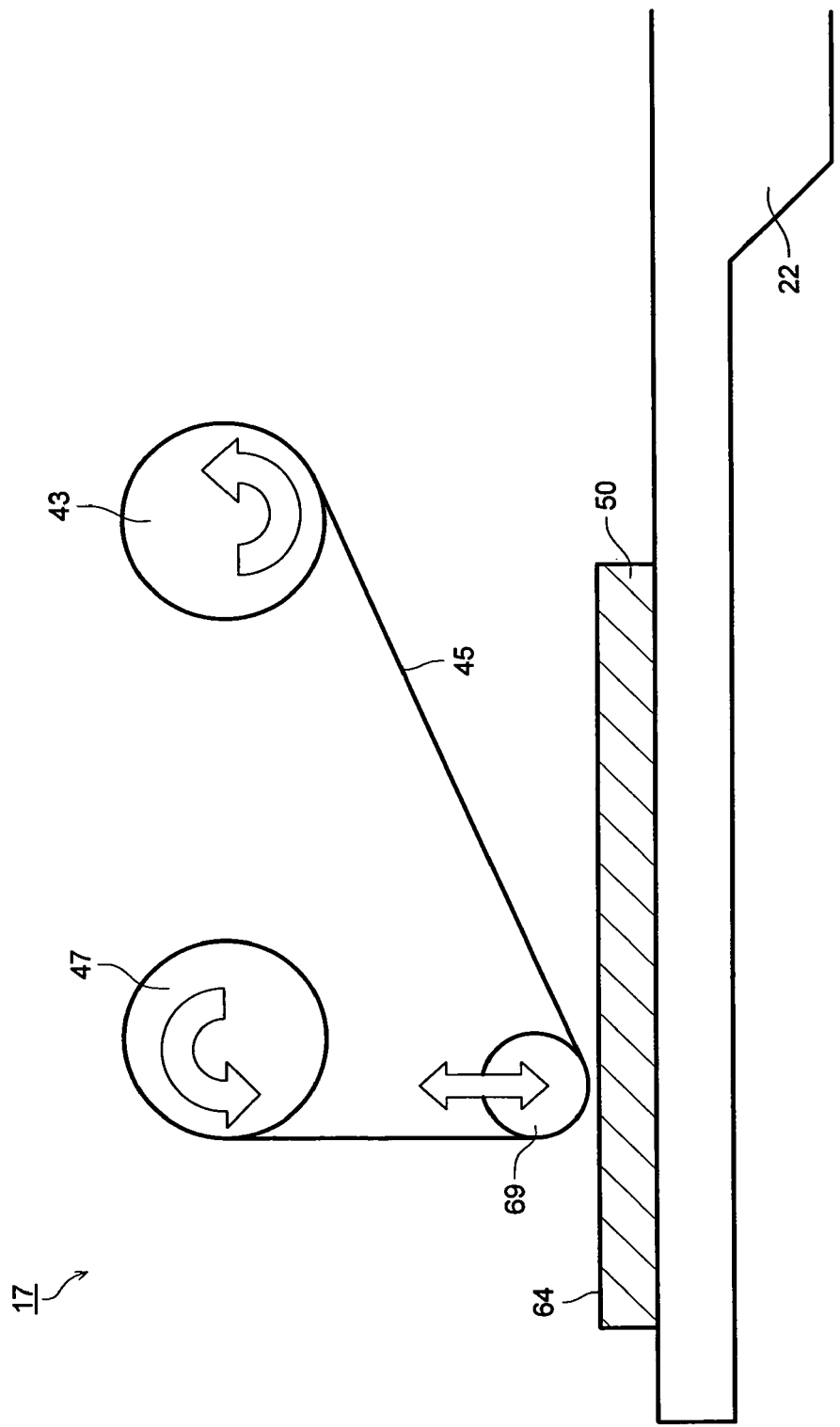
FIG. 21 is a partial schematic diagram illustrating another wiping device of the micro-overall-analysis system of the example in FIG. 1.

FIG. 21 is one showing another example of the wiping device of the micro-overall-analysis system of the invention.

The wiping device 17 of this kind is provided with wiping sheet supply roll 47 on which wiping sheet 45 for wiping liquids and foreign substances off is wound, take-up reel 43 that takes up the wiping sheet 45 at prescribed timing and with elevating device 69 which is provided between the wiping sheet supply roll 47 and the take-up reel 43 and is capable of moving the wiping sheet 45 to a prescribed position.

In the micro-overall-analysis system 10 of the present example, the testing chip 50 placed on testing chip conveyance tray 22 is constituted so that pump connecting section 64 of the testing chip 50 may be wiped by wiping device 17 in advance before the testing chip 50 is connected to micro-pump unit 26.

Further, in the wiping device 17, the wiping sheet 45 is made to have always a constant tension by the wiping sheet supply roll 47, the elevating device 69 and the take-up reel 43.

The wiping device 17 of this kind is constructed so that the elevating device 69 may descend toward the pump connecting section 64 when the pump connecting section 64 of the testing chip 50 comes to a point right under the elevating device 69, whereby, the wiping sheet 45 goes down to the pump connecting section 64 of the testing chip 50, and liquids and contaminations sticking to the pump connecting section 64 are wiped off accordingly.

As a material of the wiping sheet 45, there is no limit in particular, but resins having water-absorbing property are preferable.

As the resins having water-absorbing property, polyvinyl alcohol, poly hydroxyethyl methacrylate and polyethylene glycol are preferably used, and more preferable to be used is moisture-absorbing resin such as polyvinyl alcohol/polyacrylic acid high moisture absorbing polymer, or starch/grafted polyacrylic acid.

As another example, sponge can also be used for wiping sheet 45.

As a material for this sponge, there is no limit in particular, but sponge made of polyurethane, nonwoven fabric or nylon may be preferably used.

If the wiping sheet 45 made of moisture-absorbing resin or of sponge is used, liquids and foreign substances can surely be held, and it is possible to prevent surely that liquids and foreign substances leak out to the inside of the system main body.

The wiping device 17 which has completed wiping of pump connecting section 64 retreats to a position determined in advance, so that it may not interfere with testing chip conveyance tray 22.

In this case, it is possible to arrange so that the whole of the wiping device 17 retreats totally, or it is possible to arrange so that only elevating device 69 in the wiping device 17 goes up to retreat.

Further, in the wiping device 17 of this kind, take-up reel 43 makes predetermined number of turns after completion of each wiping so that pump connecting section 64 of testing chip 50 may be wiped with a fresh surface of wiping sheet 45 continually.

With this structure, it is possible to prevent that liquids and foreign substances removed through wiping stick to pump connecting section 64 of succeeding testing chip 50.

Further, after the whole of wiping sheet 45 in wiping sheet supply roll 47 is collected on take-up reel 43, used wiping sheet 45 collected on the take-up reel 43 is removed from the take-up reel 43 for disposal.

Then, wiping of the pump connecting section 64 can be carried out again after fresh wiping sheet supply roll 47 is installed.

Figure 22:
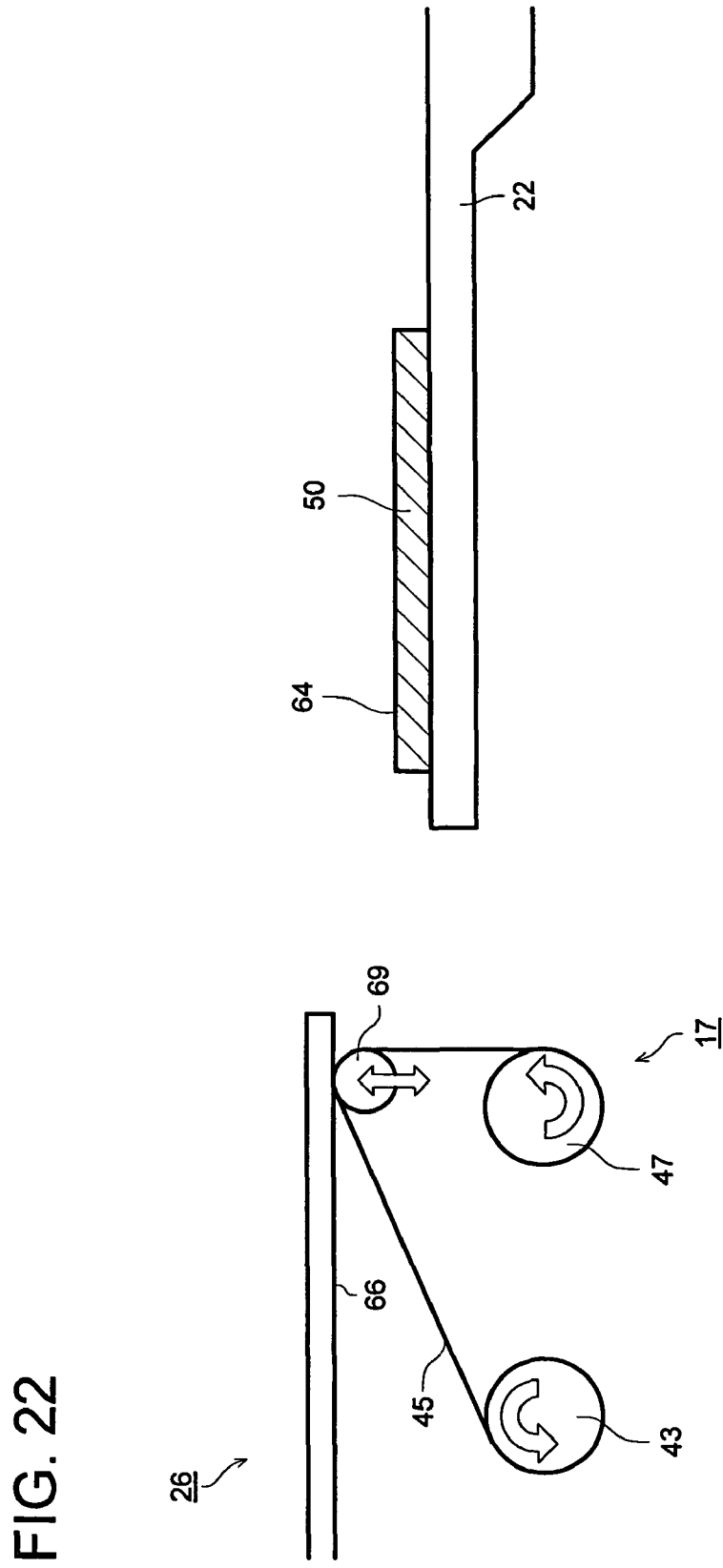
FIG. 22 is a partial schematic diagram illustrating still another wiping device of the micro-overall-analysis system of the example in FIG. 1.

Further, wiping device 17 may also be arranged so that testing chip connecting section 66 of micro-pump unit 26 may be wiped, as shown in FIG. 22.

The wiping device 17 of this kind can remove liquids and contaminations on the pump connecting section 64 when elevating device 69 moves up and down in the same way as in the wiping device 17 shown in FIG. 21.

In addition, the wiping device 17 can also be provided on each of both sides including the pump connecting section 64 side and the testing chip connecting section side, so that both sides of pump connecting section 64 of testing chip 50 and testing chip connecting section 66 of micro-pump unit 26 may be wiped.

With this structure, it is possible to wipe off liquids and foreign substances sticking to pump connecting section 64 and to testing chip connecting section 66, more surely.

Incidentally, although a framework is constituted so that wiping operations for pump connecting section 64 and testing chip connecting section 66 are conducted when testing chip conveyance tray 22 operates, in the aforesaid examples, the invention is not limited to this, and it is possible to constitute a framework wherein pump connecting section 64 and testing chip connecting section 66 are wiped when the wiping device 17 moves from front to back and from side to side.

What is claimed is:

1. An analyzer for analysis of a specimen in a testing chip that includes a micropump connecting section that is connected with a micropump to take in liquid from the micropump and includes a micro flow channel in which a reagent and the specimen are mixed so as to react with each other, the analyzer comprising:

a mounting section for mounting the testing chip attachably and detachably thereto;
a micropump unit comprising:
   a testing chip connecting section to be connected with the micropump connecting section of the testing chip which is mounted on the mounting section;
   the micropump having an inner channel therein; and
   a first flow channel which has a first end directly connected to an outlet of the micropump and a second end positioned on the testing chip connecting section so as to connect the outlet of the micropump and the testing chip connecting section to feed liquid from the outlet to the testing chip through the testing chip connecting section, when the testing chip is mounted on the mounting section;
a pressing mechanism that presses the micropump connecting section and the testing chip connecting section against each other, the connecting sections being connected with each other;
a detection device which detects a reaction in the micro flow channel; and
a cleaning mechanism which cleans the micropump connecting section and/or the testing chip connecting section, the cleaning mechanism comprising:
a gas blower that sends gas to a connecting part between the micropump connecting section and the testing chip connecting section before the micropump connecting section and the testing chip connecting section become separated from each other, wherein the micropump unit further comprises a second flow channel for at least one of sending gas sent out from the gas blower to the connecting part and taking out the liquid from the connecting part, the liquid being pressed by gas sent out from the gas blower,
wherein the second flow channel is connected directly to the first flow channel at a connection point positioned downstream of the first end and upstream of the second end in a liquid feed direction, and
wherein the testing chip connecting section comprises a contacting surface which keeps liquid-tight by being pressed against a contacting surface of the micropump connecting section by the pressing mechanism.

2. The analyzer of claim 1, further comprising at least one of:
   a pump controller to control feeding of liquid by the micropump unit; and
   a temperature controller to set a temperature of a predetermined part of the testing chip to a predetermined temperature or wherein the mounting section is a conveying tray which is moved to convey the testing chip.

3. The analyzer of claim 2, wherein the pressing mechanism is arranged at the detection section that detects reaction in the micro flow channel, the temperature controller, the micropump unit, or the conveying tray.

4. The analyzer of claim 2, wherein the pressing mechanism is structured by the detection section that detects reaction in the micro flow channel, the temperature controller, the micropump unit, or the conveying tray, each itself.

5. The analyzer of claim 2, wherein the pressing mechanism is structured by a member different from any one of the detection section, the temperature controller, the micropump unit, and the conveying tray.

6. The analyzer of claim 2 comprising the conveying tray, wherein the pressing mechanism is disposed between one of the detection section, the temperature controller and the micropump unit, and the conveying tray.

7. The analyzer of claim 1, wherein the pressing mechanism comprises a positioning structure.

8. The analyzer of claim 7, wherein the positioning structure is guided in moving by a guide groove formed on either the testing chip or the analyzer.

9. The analyzer of claim 7, wherein the positioning structure is arranged with holes formed through the testing chip and the micropump unit and a pin member to be inserted in the holes.

10. The analyzer of claim 7, wherein the positioning structure is arranged with a notch formed on a portion of a side of the testing chip and a protrusion.

11. The analyzer of claim 1, wherein the pressing mechanism is used with a sealing member deformable by compression.

12. The analyzer of claim 1,
   wherein the mounting section is a conveying tray which is moved to convey the testing chip and
   wherein the pressing mechanism is structured such that the testing chip connecting section and the conveying tray in the analyzer are sandwiched by a member.

13. The analyzer of claim 1, further comprising
   a liquid collection device connecting section provided on the micropump unit; and
   a liquid collection device that is connected to the liquid collection device connecting section and recovers liquid that has been pushed outside the micropump unit by the gas sent out from the gas blower.

14. The analyzer of claim 1, wherein a hydrophobic layer is provided on a surface of the micropump connecting section of the testing chip and/or a surface of the testing chip connecting section of the micropump unit.

15. The analyzer of claim 14, wherein the hydrophobic layer is made of any one of polyethylene, silicone and polytetrafluoroethylene.

16. The analyzer of claim 1, wherein the cleaning mechanism further comprises a surface cleaning mechanism, the surface cleaning mechanism being operable to clean the contacting surface of the micropump connecting section and/or the contacting surface of the testing chip connecting section.

17. The analyzer of claim 16, wherein the surface cleaning mechanism comprises a wiper that wipes off foreign matter and/or liquid on a surface of the micropump connecting section of the testing chip and/or a surface of the testing chip connecting section of the micropump unit.

18. The analyzer of claim 16, wherein the surface cleaning mechanism further comprises a surface cleaning gas blower, the surface cleaning gas blower being operable to remove foreign matter and/or liquid on a surface of the micropump connecting section of the testing chip and/or a surface of the testing chip connecting section of the micropump unit by sending gas.

19. The analyzer of claim 16, wherein the surface cleaning mechanism is provided adjacent to a connecting part between the testing chip and the micropump unit in the analyzer.

20. The analyzer of claim 16, the surface cleaning mechanism comprising:
   a wiping sheet for wiping a liquid and a foreign substance off;
   a wiping sheet supply roll on which the wiping sheet is wound;
   a take-up reel which takes up the wiping sheet at prescribed timing; and
   an elevating device which is provided between the wiping sheet supply roll and the take-up reel and which is capable of moving the wiping sheet to a prescribed position.

21. The analyzer of claim 16, wherein the surface cleaning mechanism is provided at a testing chip gateway for introducing the testing chip into the analyzer.

22. The analyzer of claim 21, wherein according to a movement of the introducing for the testing chip into the analyzer, a part of the surface cleaning mechanism slides on the contacting surface of the micropump connecting section.

23. The analyzer of claim 1, wherein the second flow channel is used both to send gas to the connecting part and to take out the liquid from the connecting part by switching the gas blower freely, and wherein the switching makes the gas blower capable of being used on both a micropump unit side and a testing chip side.

24. An analyzer for analysis of a specimen in a testing chip that includes a micropump connecting section that is connected with a micropump to take in liquid from the micropump and includes a micro flow channel in which a reagent and the specimen are mixed so as to react with each other, the analyzer comprising:
- a mounting section for mounting the testing chip attachably and detachably thereto;
- a micropump unit that has a testing chip connecting section to be connected with the micropump connecting section of the testing chip which is mounted on the mounting section, and feeds liquid to the testing chip through the testing chip connecting section, the micropump unit including the micropump;
- a pressing mechanism that presses the micropump connecting section and the testing chip connecting section against each other, the connecting sections being connected with each other;
- a detection device which detects a reaction in the micro flow channel; and
- a cleaning mechanism which cleans the micropump connecting section and/or the testing chip connecting section, the cleaning mechanism comprising:
- a gas blower that sends gas to a connecting part between the micropump connecting section and the testing chip connecting section before the micropump connecting section and the testing chip connecting section become separated from each other, wherein the micropump unit comprises a flow channel to send the gas sent out from the gas blower to the connecting part,
- wherein the testing chip connecting section comprises a contacting surface which keeps liquid-tight by being pressed against a contacting surface of the micropump connecting section by the pressing mechanism and,
- wherein the cleaning mechanism further comprises a surface cleaning mechanism, the surface cleaning mechanism being operable to clean the contacting surface of the micropump connecting section and/or the contacting surface of the testing chip connecting section.

* * * * *